(12) United States Patent
Micalizio et al.

(10) Patent No.: US 9,963,481 B2
(45) Date of Patent: May 8, 2018

(54) CHIRAL OLIGOMERIC PENTENOATE AMIDES AS BIO-OLIGOMER MIMETICS

(75) Inventors: Glenn C. Micalizio, Palm Beach Gardens, FL (US); Thomas Kodadek, Jupiter, FL (US); Mohosin Sarkar, Palm Beach Gardens, FL (US)

(73) Assignee: The Scripps Research Institute, La Jolla, CA (US)

( * ) Notice: Subject to any disclaimer, the term of this patent is extended or adjusted under 35 U.S.C. 154(b) by 454 days.

(21) Appl. No.: 14/343,426

(22) PCT Filed: Sep. 7, 2012

(86) PCT No.: PCT/US2012/054135
§ 371 (c)(1),
(2), (4) Date: May 21, 2014

(87) PCT Pub. No.: WO2013/036753
PCT Pub. Date: Mar. 14, 2013

(65) Prior Publication Data
US 2014/0271488 A1  Sep. 18, 2014

Related U.S. Application Data

(60) Provisional application No. 61/531,810, filed on Sep. 7, 2011.

(51) Int. Cl.
*C07K 5/08* (2006.01)
*A61K 31/19* (2006.01)
(Continued)

(52) U.S. Cl.
CPC ............... *C07K 5/08* (2013.01); *A61K 31/19* (2013.01); *A61K 31/192* (2013.01); *A61K 38/06* (2013.01); *A61K 45/06* (2013.01); *C07B 53/00* (2013.01); *C07C 51/00* (2013.01); *C07C 57/52* (2013.01); *C07C 57/54* (2013.01); *C07C 57/60* (2013.01); *C07C 57/64* (2013.01); *C07D 405/10* (2013.01); *C07D 405/14* (2013.01); *C07K 5/0205* (2013.01); *C07K 5/0804* (2013.01); *G01N 33/5008* (2013.01); *C07B 2200/07* (2013.01);
(Continued)

(58) Field of Classification Search
CPC ...... A61K 31/19; A61K 31/192; A61K 38/06; A61K 45/06; C07B 2200/07; C07B 2200/11; C07B 53/00; C07C 51/00; C07C 57/52; C07C 57/54; C07C 57/60; C07C 57/64; C07D 405/10; C07D 405/14; C07K 5/0205
See application file for complete search history.

(56) References Cited

U.S. PATENT DOCUMENTS 2,540,071 A    1/1951    Croxall et al.
6,448,409 B1   9/2002    Silks, III
(Continued)

FOREIGN PATENT DOCUMENTS

WO    WO2013036753    3/2013

OTHER PUBLICATIONS

Fernandez-Zertuche, M. et al, "Generation of alkoxyalkynyketenes from a bicyclic precursor. Cycloaddition chemistry with alkynes and theoretical studies regarding the formation of five-verses six-membered ring products", Org, Chem in Mexico, ARKAT, USA, v.11, pp. 89-99, (2003).

(Continued)

*Primary Examiner* — Valerie Rodriguez-Garcia
(74) *Attorney, Agent, or Firm* — Geoffrey K. Cooper; Thomas Fitting

(57) ABSTRACT

Chiral oligomeric pentenoate amides are bio-oligomer mimetics possessing a high degree of conformation rigidity. Conformational rigidity is desirable in the design of molecules with high affinities for biological receptors and enzymes. Libraries of such oligomeric mimetics, such as of chiral oligomeric pentenoate amides can be used to probe biological systems. The present invention provides a method for preparation of chiral oligomeric pentanoate amides comprising conversion of a chiral oxazolidinone (4)

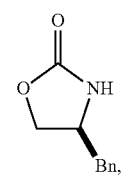

(4)

to a chiral monomer of formula (1)

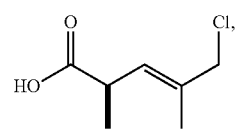

(1)

which can be oligomerized to a chiral compound of formula (12)

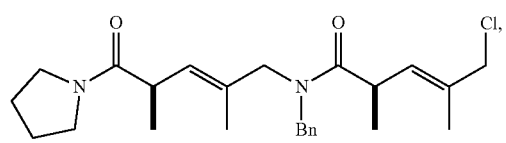

(12)

and so forth.

3 Claims, 12 Drawing Sheets

(51) Int. Cl.
| | |
|---|---|
| A61K 45/06 | (2006.01) |
| C07D 405/14 | (2006.01) |
| C07D 405/10 | (2006.01) |
| C07B 53/00 | (2006.01) |
| C07C 57/52 | (2006.01) |
| C07C 57/60 | (2006.01) |
| C07C 57/64 | (2006.01) |
| A61K 31/192 | (2006.01) |
| A61K 38/06 | (2006.01) |
| C07C 51/00 | (2006.01) |
| C07K 5/02 | (2006.01) |
| C07K 5/083 | (2006.01) |
| G01N 33/50 | (2006.01) |
| C07C 57/54 | (2006.01) |

(52) U.S. Cl.
CPC .. C07B 2200/11 (2013.01); G01N 2800/7028 (2013.01)

(56) References Cited

U.S. PATENT DOCUMENTS

| | | |
|---|---|---|
| 7,314,731 B2 | 1/2008 | Kornblith |
| 2005/0182235 A1 | 8/2005 | Zhong et al. |
| 2006/0247448 A1 | 11/2006 | Boivin et al. |
| 2009/0175888 A1 | 7/2009 | Ng et al. |
| 2011/0052641 A1 | 3/2011 | Mardi et al. |

OTHER PUBLICATIONS

Tan, D., "Diversity-oriented synthesis: exploring the intersections between chemistry and biology", Nat. Chem. Biol., V. 1, pp. 74-84, (2005).
Spiegel, D. et al, "An oligomer-based approach to skeletal diversity in small-molecule synthesis", J. Amer. Chem. Soc., v. 128, pp. 14766-14767, (2006).
Nielsen, T. et al, "Towards the optimal screening collection: a synthesis strategy", Angew. Chem. Int., Ed., v. 47, pp. 48-56, (2008).
Udugamasooriya, D. et al, "A peptide 'Antibody Surrogate' that antagonizes VEGF receptor 2 activity", J. Am. Chem, Soc., 130:17:5744-5752, (Apr. 30, 2008).
Hoffman, R., "Flexible molecules with defined shape-conformational design", Angew. Chem. Int., Ed. v. 31, pp. 1124-1134, (1992).
Houghten, R., "General method for the rapid solid-phase synthesis of large number of peptides: Specificity of antigen-antibody interaction at the level of individual amino acids", Proc. Natl. Acad., Sci. USA, v. 82, pp. 5131-5135, (Mar. 29, 1985).
Evans, D. et al, "Diastereoselective magnesium halide-catalyzed anti-Aldol reactions of Chiral N-Acyloxaolidinones", J. Am. Chem. Soc., v. 124, pp. 392-393, (2002).
Ravikumar, P. et al, "Allylic and Allenic halide synthesis via NbCl5- and NbBr5-mediated alkoxide rearrangements", J. Org. Chem., v. 74, pp. 7294-7299, (2009).
Hoffman, R., "Conformation design of open-chain compounds", Angew. Chem. Intl. Ed., v.39, pp. 2054-2070, (2000).

Lim, H. et al, "Identification of a peptoid inhibitor of the Proteasome 19S regulatory particle", J. Amer, Chem. Soc., v.129, pp. 7750-7751, (2007).
Xiao, X. et al, "Design and synthesis of a cell-permeable synthetic transcription factor mimic", J. Comb. Chem., 9:4:592-600, (May 27, 2007).
Levine, A. et al, "The first 30 years of p53: growing ever more complex", Nat. Rev. Cancer, 9:10:749-758, (2009).
Brown, C. et al, "Awakening guardian angels: drugging the p53 pathway", Nat. Rev. Cancer, v. 9, pp. 862-873, (Dec. 2009).
Cochran, A., "Antagonists of protein-protein interactions", Chem & Biol., 7:4:R85-R94, (2000).
Syka, J. et al, "Peptide and protein sequence by electron transfer dissociation mass spectrometry", Proc. Nat. Acad. Sci., USA, 10:26:9528-9533, (2004).
Lambert, J. et al, "PRIMA-1 reactivates mutant p53 by covalent binding to the core domain", Cancer Cell, 15:5:376-388, (May 2009).
Boeckler, F. et al, "Targeted rescue of a destabilized mutant of p53 by an in silico screened drug", Proc. Nat. Acad. Sci., USA, v.105, pp. 10360-10365, (2008).
Clemons, P. et al, "Small molecules of different origins have distinct distributions of structural complexity that correlate with protein-binding profiles", Proc. Nat. Acad. Sci., USA, 107:44:18787-18792, (Nov. 2, 2010).
Morton, D. et al, "Synthesis of natural-product-like molecules with over eighty distinct scaffolds", Angew. Chem. Int. Ed., v.48, pp. 104-109, (2009).
Luo, T., "Gold(I)-catalyzed coupling reactions for the synthesis of diverse small molecules using the build/couple/pair strategy", J. Am. Chem. Soc., v.131, pp. 5667-5674, (2009).
Uchida, T. et al, "Skeletally diverse small molecules using a build/couple/pair strategy", Org. Lett., 11:7:1559-1562, (2009).
Reddy, M. et al, "Identification of candidate IgG biomarkers for Alzheimer's Disease via combinational library screening", Cell, v.144, pp. 132-142, (Jan. 7, 2011).
Aquino, C. et al, "A biomimetic and Polyketide-inspired approach to small molecule ligand discovery", The Scripps Research Institute, Depts. of Chemistry, Cancer Biology, and Molecular Therapeutics, Jupiter, FL, (2012).
Rader, C. et al, "Chemically programmed monoclonal antibodies for cancer therapy: adaptor immunotherapy based on a covalent antibody catalyst", Proc. Natl. Acad. Sci., USA, v.100, pp. 5396-5400, (2003).
Murelli, R. et al, "Chemical control over immune recognition: a class of antibody-recruiting small molecules that target prostate cancer", J. of Am. Chem. Soc., 131:47:17090-17092, ((Dec. 2, 2009).
Catera, R. et al, "Chronic Lymphocytic Leukemia cells recognize conserved Epitopes associated with Apoptosis and Oxidation", Mol. Med., 14:11-12:665-674, (2008).
Zuckerman, R. et al, "Efficient method for the preparation of Peptoids {Oligo(N-substituted glycines)} by Submonomer solid-phase synthesis", J. Am. Chem. Soc., v.114, pp. 10646-10647, (1992).
Kodadek, T., "Rethinking Screening", Internet Article: www.nature.com/naturechemicalbiology, Nature Chem. Biol., v.6, pp. 1160-1163, (Mar. 2010).
Hoffmann, R., "Allylic 1,3-Strain as a controlling factor in stereoselective transformations", Chem. Rev., v. 89, pp. 1841-1860, (1989).

CHIRAL OLIGOMERIC PENTENOATE AMIDES AS BIO-OLIGOMER MIMETICS

CROSS-REFERENCE TO RELATED APPLICATIONS

This is a national stage filing in accordance with 35 U.S.C. § 371 of PCT/US2012/054135, filed Sep. 7, 2012, which claims the benefit of the priority of U.S. provisional patent application No. 61/531,810 entitled "CHIRAL COMPOUNDS OF VARYING CONFORMATIONAL RIGIDITY AND METHODS OF SYNTHESIS" filed Sep. 7, 2011, which is incorporated herein by reference in its entirety.

STATEMENT REGARDING FEDERALLY SPONSORED RESEARCH

This invention was made with government support under Grant number OD000663 awarded by the National Institutes of Health. The government has certain rights in the invention.

FIELD OF THE INVENTION

Embodiments are directed to synthesis of libraries of novel and structurally diverse chiral compounds having varying degrees of conformational rigidity. The novel compounds have many uses including diagnostics, prevention and treatment of diseases or symptoms thereof.

BACKGROUND

Oligomerization is the central synthetic strategy by which nature derives molecules with function. With only a small collection of monomeric units, and bond-forming processes compatible with the cellular environment, sequential union (oligomerization) results in great molecular and functional diversity. Examples include complex biological polymers like proteins, nucleic acids, and carbohydrates, as well as small molecule natural products (i.e. fatty acids, polyketides and terpenes). The structural diversity of products derived from oligomerization in nature is clearly vast, resulting in molecules that have a range of properties and functions. In contrast to Nature's oligomer-based approach to molecular diversification, the impressive and elegant laboratory approaches to structural diversity that define state-of-the-art synthetic solutions typically embrace strategic and divergent reactivity of complex organic intermediates (Schreiber, S. L. Target-oriented and diversity-oriented organic synthesis in drug discovery. *Science* 287, 1964-1969 (2000); Tan, D. S. Diversity-oriented synthesis: exploring the intersections between chemistry and biology. *Nat. Chem. Biol.* 1, 74-84 (2005); Spiegel, D. A. et al. An oligomer-based approach to skeletal diversity in small-molecule synthesis. *J Am. Chem. Soc.* 128, 14766-14767 (2006); Nielsen, T. E. et al. Towards the optimal screening collection: a synthesis strategy. *Angew. Chem. Int. Ed.* 47, 48-56 (2008)).

SUMMARY

This Summary is provided to present a summary of the invention and to briefly indicate the nature and substance of the invention. It is submitted with the understanding that it will not be used to interpret or limit the scope or meaning of the claims.

Embodiments are directed to synthesis of novel compounds and methods for synthesizing such compounds.

In one embodiment, a compound comprises a molecule of general structure I:

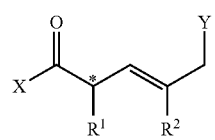

Wherein X comprises $OR^3$, $NHR^4$, H or halide; $R^3$ comprises alkyl, aryl, carboxyl; $R^4$ comprises H, $OR^3$, $NR^3{}_2$, alkyl or aryl; * is a chiral center [(R) or (S)]; $R^1$ comprises alkyl, aryl, $OR^4$; $R^2$ comprises alkyl, aryl, halo; Y comprises halide, $NHR^4$, OH, C(O)X.

Other aspects are described infra.

BRIEF DESCRIPTION OF THE DRAWINGS

FIG. 1A is a schematic showing a selection of biological and biopolymer mimetics. FIG. 1B is a schematic showing a selection of polyketide-derived natural products. FIG. 1C is a schematic showing the general structure of COPAs—chiral oligomers of N-substituted 5-amino-2,4-dialkyl-3-pentenoic amides. FIG. 1D is a schematic showing the structural features that lead to the rigidification of COPA oligomers.

FIG. 3A is a schematic showing the "submonomer" style synthesis of peptoids. FIG. 3B is a schematic showing the asymmetric synthesis of 5-chloro-2,4-dimethyl-3-pentenoic acid 1. FIG. 3C is a schematic showing the use of 1 in solution phase oligomerization. FIG. 3D shows a panel of monomers used in library synthesis. FIG. 3E is a schematic showing general information regarding resin and linker employed in solid-phase library synthesis. FIG. 3F is a schematic showing the general structure of libraries prepared from building blocks depicted in FIG. 3D—COPA and peptoid tetramers.

FIG. 4A is an embodiment of a general scheme for on-bead screening of a COPA library against the DNA binding domain of p53 (p53-DBD, residues 94 to 312) expressed with an epitope tag FLAG. TENTAGEL beads bound to p53-DBD protein were visualized under a fluorescent microscope by treating beads with anti-FLAG primary antibody and anti-IgG secondary antibody conjugated to Quantum dot emitting red fluorescent light at 655 nm. FIG. 4B: Sequence elucidation and identification of a COPA tetramer that binds to the p53-DBD. Sequence of the COPA tetramer was established by analysis of mass spectral data derived from ETD-based fragmentation. FIG. 4C shows a schematic of the fluorescence polarization assay for binding affinity of fluorescein conjugated COPA tetramer (14a) against p53-DBD, carbonic anhydrase II (CAH II from bovine erythrocyte), platelet activating factor acetyl hydrolase (PAFAHIB3), and bromodomain containing 4 (BRD4) proteins. A COPA tetramer with the same linker region and different side chains on the amide nitrogens was used as a control oligomer (co). The binding affinity of COPA tetramer to p53-DBD was determined as $K_D \sim 10$ µM.

DETAILED DESCRIPTION

Figures 1A, 1B, 1C, 1D:
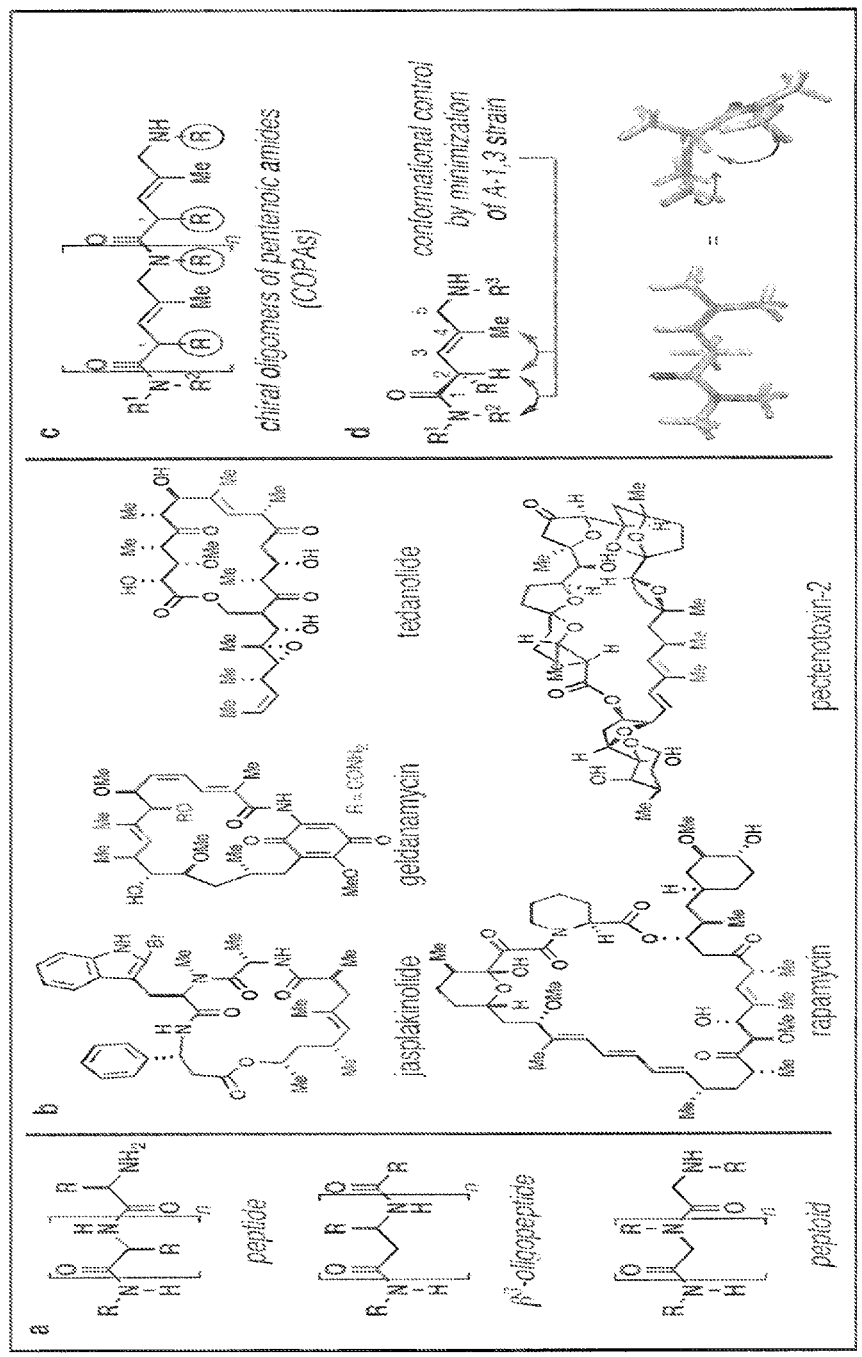
FIGS. 1A-1D are schematics showing natural and synthetic oligomers, polyketide-derived natural products, and a polyketide-inspired class of chiral and conformationally rigid synthetic oligomer.

Embodiments are directed to novel synthetic compounds and methods of synthesizing these compounds. The compounds have broad utility for use in detection and treatment of disease.

The present invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms, "compound" and "compounds" as used herein refers to a compound encompassed by the generic formulae disclosed herein, any subgenus of those generic formulae, and any forms of the compounds within the generic and subgeneric formulae. Unless specified otherwise, the term further includes the racemates and stereoisomers, of the compound or compounds.

As used herein, the term "rigid" refers to a molecule's propensity to adopt a defined conformation in preference to a variety of competing conformations. Such "rigidity" can be imparted by a variety of molecular features that provide a bias in favor of a local conformation about a molecular skeleton. Within the context of the invention, rigidification is imparted by allylic strain—a governing feature of molecular conformation that is well understood by those skilled in the art (Hoffmann, R. W. Allylic 1,3-Strain as a Controlling Factor in Stereoselective Transformations, *Chem. Rev.* 1989, 89, 1841-1860; Hoffmann, R. W. Flexible Molecules with Defined Shape-Conformational Design, *Angew. Chem. Int. Ed.*, 1992, 31, 1124-1134).

The term "rigidity" refers to the degree of flexibility of the molecule and includes the terms "flexible", "semi-rigid", "rigid" and all variations in between. The current invention provides a means of addressing the conformational rigidity of a small molecule and related oligomers that is based on introducing allylic strain in the central molecular motif depicted in FIG. 1D.

The term "chiral" is used to describe an object that is nonsuperimposable on its mirror image and therefore has the property of chirality.

The term "chirality" refers to the geometric property of a rigid object (or spatial arrangement of points or atoms) of being non-superimposable on its mirror image. If the object is superimposable on its mirror image the object is described as being achiral.

The term "chirality axis" refers to an axis about which a set of ligands is held so that it results in a spatial arrangement which is not superposable on its mirror image.

The term "chiral center" refers to an atom holding a set of ligands in a spatial arrangement, which is not superposable on its mirror image. A chirality center may be considered a generalized extension of the concept of the asymmetric carbon atom to central atoms of any element. Each chiral center (*C) is labeled R or S according to a system by which its substituents are each designated a priority according to the Cahn Ingold Prelog priority rules (CIP), based on atomic number. In some embodiments, the stereochemistry of the chiral centers (marked by "*C") represents all possible combinations in terms of relative and absolute chemistry.

The term "racemate" as used herein refers to an equimolar mixture of two optically active components that neutralize the optical effect of each other and is therefore optically inactive.

The term, "enantiomer" refers to one of a pair of optical isomers containing one or more asymmetric carbons (C*) whose molecular configurations have left- and right-hand (chiral) forms. Enantiomers have identical physical properties, except for the direction of rotation of the plane of polarized light. Enantiomers have identical chemical properties except toward optically active reagents.

The terms "solvate" or "solvates" of a compound refer to those compounds, where compounds is as defined above, that are bound to a stoichiometric or non-stoichiometric amount of a solvent. Solvates of a compound includes solvates of all forms of the compound. Preferred solvents are volatile, non-toxic, and/or acceptable for administration to humans in trace amounts. Suitable solvates include distilled and pyrogen-free water.

The term "isomer" as used herein refers to one of two or more molecules having the same number and kind of atoms and hence the same molecular weight, but differing in chemical structure. Isomers may differ in the connectivities of the atoms (structural isomers), or they may have the same atomic connectivities but differ only in the arrangement or configuration of the atoms in space (stereoisomers). "Stereoisomer" or "stereoisomers" refer to compounds that differ in the chirality of one or more stereocenters. Stereoisomers may include, but are not limited to, E/Z double bond isomers, enantiomers, and diastereomers. Structural moieties that, when appropriately substituted, can impart stereoisomerism include, but are not limited to, olefinic, imine or oxime double bonds; tetrahedral carbon, sulfur, nitrogen or phosphorus atoms; and allenic groups. Enantiomers are non-superimposable mirror images. A mixture of equal parts of the optical forms of a compound is known as a racemic mixture or racemate. Diastereomers are stereoisomers that are not mirror images.

The term "tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N-moiety such as pyrazoles, imidazoles, benzimidazoles, triazoles, and tetrazoles.

The term, "electrophile" refers to an ion or atom or collection of atoms, which may be ionic, having an electrophilic center, i.e., a center that is electron seeking, capable of reacting with a nucleophile.

The term, "nucleophile" refers to an ion or atom or collection of atoms, which may be ionic, having a nucleophilic center, i.e., a center that is seeking an electrophilic center or capable of reacting with an electrophile.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid that is capable of chemically reacting with a functional group on a different compound to form a covalent linkage. Reactive groups generally include nucleophiles, electrophiles and photoactivatable groups. Exemplary reactive groups include, but are not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids, thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds., Organic Functional Group Preparations, Academic Press, San Diego, 1989).

An "electrophilic reactive group" refers to a reactive group as described above that is capable of reaction with a nucleophile. Exemplary electrophilic reactive groups of the present invention are halide groups, such as bromide or chloride substituents, halogens (F, Cl, Br, or I); nitriles (CN); carboxylic esters (COOX) where X=a good leaving group; carbonyls (CO); carboxyl groups, -aldehydes (—CHO), acetaldehydes. Good leaving groups are well known to one of ordinary skill in the art.

The term "lower" as used herein refers to a group having between one and six carbons.

The term "substituted" as used herein refers to substitution with the named substituent or substituents, multiple degrees of substitution being allowed unless otherwise stated.

The term "alkyl" as used herein refers to a straight or branched chain monovalent or divalent hydrocarbon radical having, except where specifically indicated otherwise, from one to about fifty carbon atoms, optionally substituted with substituents including, but not limited to: halogens, halides, alkylhalides, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may contain one or more O, S, S(O), or S(O)$_2$ moieties. Examples of "alkyl" as used herein include, but are not limited to, methyl, ethyl, propyl, decyl, undecyl, octadecyl, nonadecyl, eicosyl, heneicosyl, decosyl, tricosyl, tetracosyl, and pentacosyl, n-butyl, t-butyl, n-pentyl, isobutyl, and isopropyl, and the like. In some embodiments the alkyl comprises 1, 2, 3, 4, 5, 6, 7, 8, 9, 10, 11, or 12 carbon atoms.

The term "alkenyl," as used herein, denotes a straight (unbranched) or branched hydrocarbon chain having one or more double bonds therein where the double bond can be unconjugated or conjugated to another unsaturated group (e.g., a polyunsaturated alkenyl) and can be unsubstituted or substituted, with multiple degrees of substitution being allowed. For example, halides, alkylhalides, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may contain one or more O, S, S(O), or S(O)$_2$ moieties. For example, and without limitation, the alkenyl can be vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, decenyl, undecenyl, dodecenyl, heptadecenyl, octadecenyl, nonadecenyl, eicosenyl, heneicosenyl, docosenyl, tricosenyl, tetracisenyl, pentacosenyl, phytyl, the branched chain isomers thereof, and polyunsaturated alkenes including octadec-9,12,-dienyl, octadec-9,12,15-trienyl, and eicos-5,8,11,14-tetraenyl.

The term "alkynyl" refers to a hydrocarbon radical having from about two to about fifty carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or S(O)$_2$ moieties.

The term "aryl" as used herein refers to an optionally substituted benzene ring or to an optionally substituted benzene ring system fused to one or more optionally substituted benzene rings, with multiple degrees of substitution being allowed. Substituents include, but are not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, amino sulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-napthyl, 1-naphthyl, 1-anthracenyl, and the like.

It should be understood that wherever the terms "alkyl" or "aryl" or either of their prefix roots appear in a name of a substituent, they are to be interpreted as including those limitations given above for alkyl and aryl. Designated numbers of carbon atoms (e.g., $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

The terms "carbamates" or "urethanes" as used herein refer to a group of organic compounds sharing a common functional group having the general structure —NR(CO)O—.

As used herein, "cycloalkyl" (used interchangeably with "aliphatic cyclic" herein) refers to an alicyclic hydrocarbon group optionally possessing one or more degrees of unsaturation, having from about three to about fifty carbon atoms, optionally substituted with substituents, for example: halogens, halides, alkylhalides, selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

The terms "heterocycle" and "heterocyclic" as used herein are used interchangeably to refer to a three to about twelve-membered heterocyclic ring optionally aromatic or possessing zero, one- or more degrees of unsaturation, containing one or more heteroatomic substitutions, for example: —S—, —SO—, —SO$_2$—, —O—, or —N— and substituents including, but not limited to, halogens, halides, alkylhalides lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring optionally may be fused to one or more of another "heterocyclic," cycloalkyl or aryl ring(s).

"Cells of the immune system" or "immune cells", is meant to include any cells of the immune system that may be assayed, including, but not limited to, B lymphocytes, also called B cells, T lymphocytes, also called T cells, natural killer (NK) cells, natural killer T (NK) cells, lymphokine-activated killer (LAK) cells, monocytes, macrophages, neutrophils, granulocytes, mast cells, platelets, Langerhan's cells, stem cells, dendritic cells, peripheral blood mononuclear cells, tumor-infiltrating (TIL) cells, gene modified immune cells including hybridomas, drug modified immune cells, antigen presenting cells and derivatives, precursors or progenitors of the above cell types.

The term "hematopoietic malignancy" refers to a cancer or hyperproliferative disorder generated during hematopoiesis involving cells such as leukocytes, lymphocytes, natural killer cells, plasma cells, and myeloid cells such as neutrophils and monocytes. Hematopoietic Malignancies include the diseases listed in the WHO classification of Human Hematopoietic Malignancies; Tumors of Hematopoietic and Lymphoid Tissues (Jaffe E. S., Harris N. L., Stein H., Vardiman J. W. (Eds.) (2001): World Health Organization Classification of Tumours. Pathology and Genetics of Tumours of Hematopoietic and Lymphoid Tissues. IARC Press: Lyon) with the morphology code of the International Classification of Diseases (ICD-O). Behavior is coded/3 for malignant tumors and/i for lesions of low or uncertain malignant potential.

The term "cancer" refers to or describes the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, and villous colon adenoma "Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with compositions comprising Formula I compounds, encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhan's cells, and endothelial cells). It will be appreciated by persons skilled in the art that the activation of one or a combination of these phenotypes in these cells can contribute to the initiation, perpetuation, or exacerbation of an inflammatory disorder.

The term "specifically binds" to a target molecule, such as for example, an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. For example, an antibody "specifically binds" or "preferentially binds" to a target if it binds with greater affinity, avidity, more readily, and/or with greater duration than it binds to other substances. It is also understood by reading this definition that; for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

As used herein, a "pharmaceutically acceptable" component/carrier etc is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

The term "prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. A general overview of prodrugs is provided in T. Higuchi and V. Stella, *Pro-drugs as Novel Delivery Systems*, Vol. 14 of the A.C.S. Symposium Series, and in Edward B. Roche, ed., Bioreversible The term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), *Handbook of Pharmaceutical Salts Properties*, Selection, and Use; 2002.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, "biological samples" include solid and body fluid samples. The biological samples used in the present invention can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils, thymus and skin, or samples taken from tumors. Examples of "body fluid samples" include, but are not limited to blood, serum, semen, prostate fluid, seminal fluid, urine, feces, saliva, sputum, mucus, bone marrow, lymph, and tears.

The term "high-throughput screening" or "HTS" refers to a method drawing on different technologies and disciplines, for example, optics, chemistry, biology or image analysis to permit rapid, highly parallel biological research and drug discovery. HTS methods are known in the art and they are generally performed in multiwell plates with automated liquid handling and detection equipment; however it is also envisioned that the methods of the invention may be practiced on a microarray or in a microfluidic system.

Compositions

Attempts to emulate Nature's strategy for creation of structural and functional diversity in a synthetic vein have resulted in the creation of many interesting compound classes, including β-peptides, peptoids, and peptide nucleic acids (FIG. 1A). A substantial value associated with these bio-inspired oligomers is their compatibility with split-and-pool solid phase synthesis (Houghten, R. A. *Proc. Natl. Acad. Sci. USA*, 82, 5131-5135 (1985)), a powerful technology for the creation of large and diverse chemical libraries. However, a common limitation with these existing classes of unnatural oligomers is that they lack the conformational constraints typical of small molecule natural products, a property that likely limits their affinity for biological targets due to entropic penalties that result from assuming a particular bound conformation.

In a preferred embodiment, a compound comprises the structure represented by general Formula I:

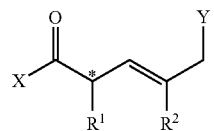

I

Wherein, the termini X and Y can be suitably reactive to allow for bidirectional functionalization.

The compound represented by general Formula I provides a rigid chiral motif for controlling the three-dimensional orientation of $R^1$ and $R^2$ with respect to each other as well as COX and $CH_2Y$. For example, if X=OH, the carboxylic acid may be used for amide bond formation with a variety of amines. Likewise, if Y=Cl, nucleophilic displacement with primary amines would deliver secondary allylic amine products. X—C=O is more reactive than $CH_2Y$, such that addition of two nucleophiles can be controlled and a defined head to tail oligomer can be synthesized. Thus, COX and $CH_2Y$ are functionalities that may be used to increase the size of the molecule by suitable intermolecular reactions at these sites. Without limitation, $R^1$ and $R^2$ comprise, all saturated, partially saturated and unsaturated hydrocarbons. The saturated hydrocarbons include all alkanes, that is, linear branched or cyclic structures, monovalent or polyvalent, substituted, partially substituted or combinations thereof. Examples of substitutions include, without limitation, N, O, Si, P, S, $NH_2$, $NH_3$, N-oxides, S-oxides alkyl, aryl, carboxyl, arylalkyl, cycloalkyl, cycloheteroalkyl, heteroalkyl, heteroaryl or heteroarylalkyl group; and, the like, as long as the substitutions are compatible with the method of synthesis and/or can be introduced to the $R_1$ and $R_2$ groups post synthesis.

In a preferred embodiment, compounds of general Formula I may be employed in oligomerization processes to generate higher molecular weight species. Such oligomerization chemistry can proceed by stepwise union of compounds of Formula I (i.e. FIG. 1C and FIG. 2), or through coupling to other monomeric building blocks—the nature of the building blocks appended in such fashion will relate to the precise nature of the compound generalized by Formula I (i.e. when X=OH, and Y=NHR, a range of compounds including, but not limited to carboxylic acids). In the case of an oligomerization process that employs the general compound depicted in Formula I, displacement of an allylic chloride (Y=Cl) with a suitable nucleophile (i.e. including but not limited to a primary amine, hydrazine, OH, etc), followed by acylation with another molecule of general Formula I (or a different suitable acylating agent) would deliver complex synthetic oligomers [one of the many generic structures possible could be depicted as $(XCO—*CHR^1—CH—CR^2CH_2Y)_{(n+1)}$ wherein n is equal to or greater than 1, and * is a chiral center [(R) or (S)]— for oligomers that have a "mixed" backbone (defined by inclusion of alternative building blocks in addition to compounds of general Formula I), a simple generic structure is not possible to clearly depict the great potential of this chemistry to access diverse molecules—for example, $(XCO—*CHR^1—CH—CR^2CH_2Y)_{(1)}(COCH_2Y)_{(2)}$ $(XCO—*CHR^1—CH—CR^2CH_2Y)_{(1)}$ (where $Y=NR^3$) would correspond to a tetramer where the first residue is composed of compound shown by Formula I, the second and third residues derive from incorporation of bromoacetic acid, and the fourth residue derives from another unit of Formula 1].

While oligomerization of compounds similar to Formula I (i.e. X=OH; Y=Cl) is thought to define a particularly powerful use of its reactivity to generate complex and diverse libraries of chiral and conformationally restricted molecules of potential utility as therapeutic agents and diagnostics, or as components of such agents, other embodiments of the current invention include the general use of units of Formula 1 as a chiral scaffold to display chemical information about its core structure. Here, "chemical information" refers to the nature of the substituents X, $R^1$, $R^2$, and Y, held about the five-carbon backbone. [X, $R^1$, $R^2$, and Y have already been defined]. This backbone defines a readily accessible skeleton to display building block functionality in defined regions of three dimensional space based on the minimization of simple non-bonded steric interactions (i.e. allylic strain).

Figure 11:
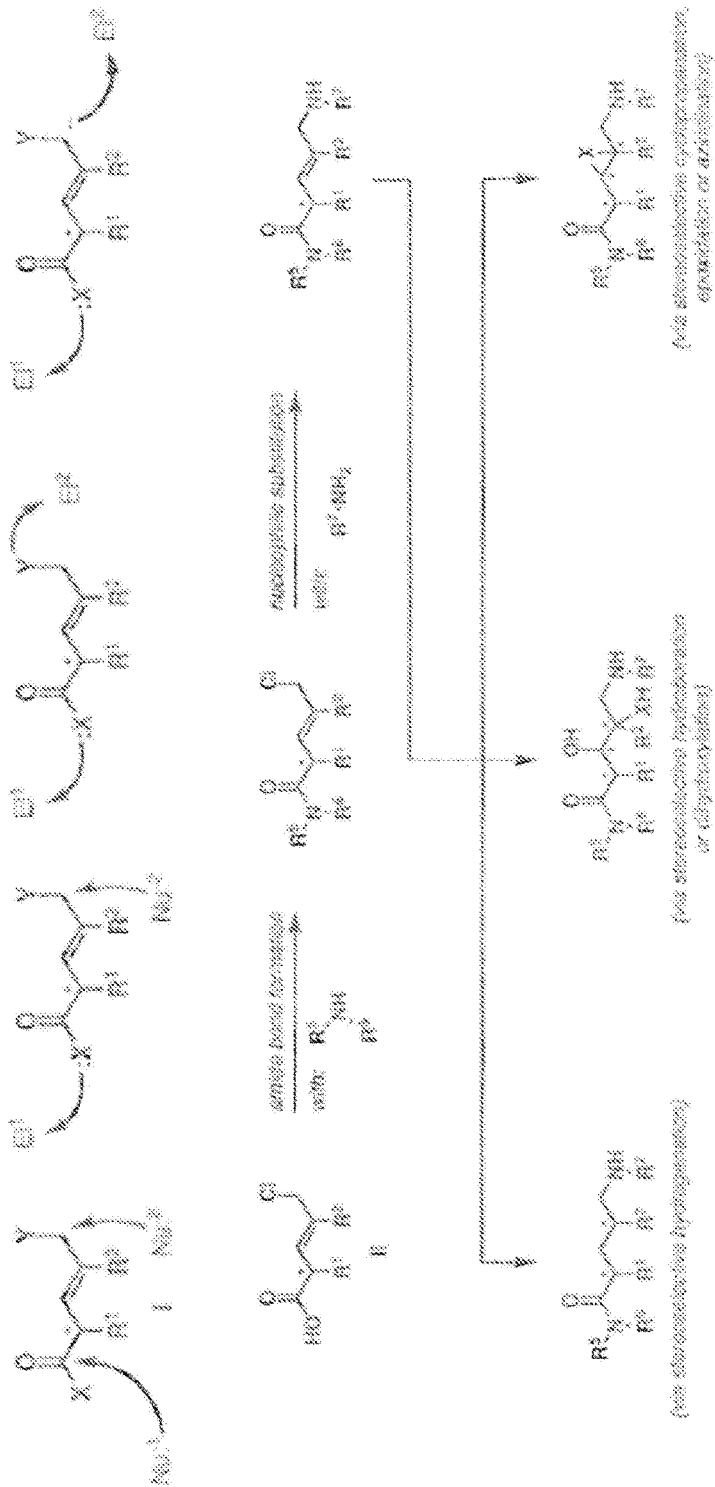
FIG. 11 is a schematic representation showing that the compound of general Formula I may function as a bifunctional reagent and partake in a variety of mono- and bi-directional homologation chemistry based on the nature of substituents X and/or Y wherein either terminus can serve as a nucleophilic or electrophilic motif. The chloroacid, shown by representative Formula II was used in sequential amide bond forming reaction and nucleophilic displacement, wherein Nu is a nucleophile and El is an electrophile.

The compound of general Formula I may function as a bifunctional reagent and partake in a variety of mono- and bi-directional homologation chemistry based on the nature of substituents X and/or Y wherein either terminus can serve as a nucleophilic or electrophilic motif. By way of example, this is illustrated in the general reaction Scheme shown in FIG. 11. This example is for illustrative purposes only and is not meant to be limiting or construed as such. The chloroacid, shown by representative Formula II was used in sequential amide bond forming reaction and nucleophilic displacement, wherein Nu is a nucleophile and El is an electrophile; $R^1$ and $R^2$ are as previously described.

$R^5$ independently comprises any functionality that does not interfere with the ability to perform the given chemical homologation defined in this case by: 1) amide bond formation, and 2) nucleophilic substitution (displacement of the allylic chloride). Examples of such functionality include, but are not limited to alkyl, aryl, heteroaryl, $NR^5R^{5'}$, $OR^5$.

$R^6$ independently comprises any functionality that does not interfere with the ability to perform the given chemical homologation defined in this case by: 1) amide bond formation, and 2) nucleophilic substitution (displacement of the allylic chloride). Examples of such functionality include, but are not limited to alkyl, aryl, heteroaryl, $NR^5R^6$, $OR^5$).

$R^7$ independently comprises any functionality that does not interfere with the ability to perform the given chemical homologation defined in this case by: 1) amide bond formation, and 2) nucleophilic substitution (displacement of the allylic chloride). Examples of such functionality include, but are not limited to alkyl, aryl, heteroaryl, $NR^5R^6$, $OR^5$).

Due to the ready availability of stereoselective transformations of the central substituted alkene, a variety of stereo defined products can be prepared from this starting material, e.g. hydrogenation, hydroboration, dihydroxylation, cyclopropanation, epoxidation, etc. Further, the compounds produced from the homologation of such building blocks, or via other routes represent a class of compounds with unique and diverse properties.

The monomers of Formula I allow for the introduction of a broad range of substructures, positioned in a defined region of 3-dimensional space with respect to one another.

In one embodiment, the one or more units comprise substitutions which are independent of a previous unit's substitutions. For example in one unit, $R^1$ can be an alkyl and in another unit $R^1$ is an aryl.

In a preferred embodiment, where molecules of general Formula I are employed in a controlled oligomerization (to result in dimers, trimers, tetramers, and higher oligomeric structures), the local conformational preferences that result from incorporating these chiral subunits is reminiscent of the motifs commonly observed in bioactive natural products from polyketide biosynthetic origin (FIG. 1B). Members of this natural product class often contain relatively simple stereochemically defined structural motifs that participate in dictating the overall conformational preferences of the molecule.

In a preferred embodiment reflecting the role that unsaturated stereodefined motifs play in governing the conformational dynamics of polyketide-derived natural products, a method of synthesizing oligomers of molecules of general Formula I has been realized to afford a biomimetic polyketide-inspired approach to the synthesis of diverse libraries of chiral and conformationally restricted small molecules. These oligomers, termed "COPAs" (chiral oligomers of pentoic amides) comprise a central N-substituted 5-amino 2,4-dialkyl-3-pentenoic amide motif to provide a chiral environment about each monomeric unit. The control of conformation resulting from this motif is substantial, and is based on the minimization of non-bonded steric interactions about the α-branched trisubstituted alkene and α-branched tertiary amide. As illustrated in FIG. 1D, each of these structural motifs imparts substantial rigidification, as the C2 proton is constrained to being roughly in-plane with the C4-alkyl group, and $R^2$-amide substituent—defining a rigid chiral environment at each monomer, where the amide and alkyl substitution emerging from this core are positioned in three-dimensional space.

Figure 2:
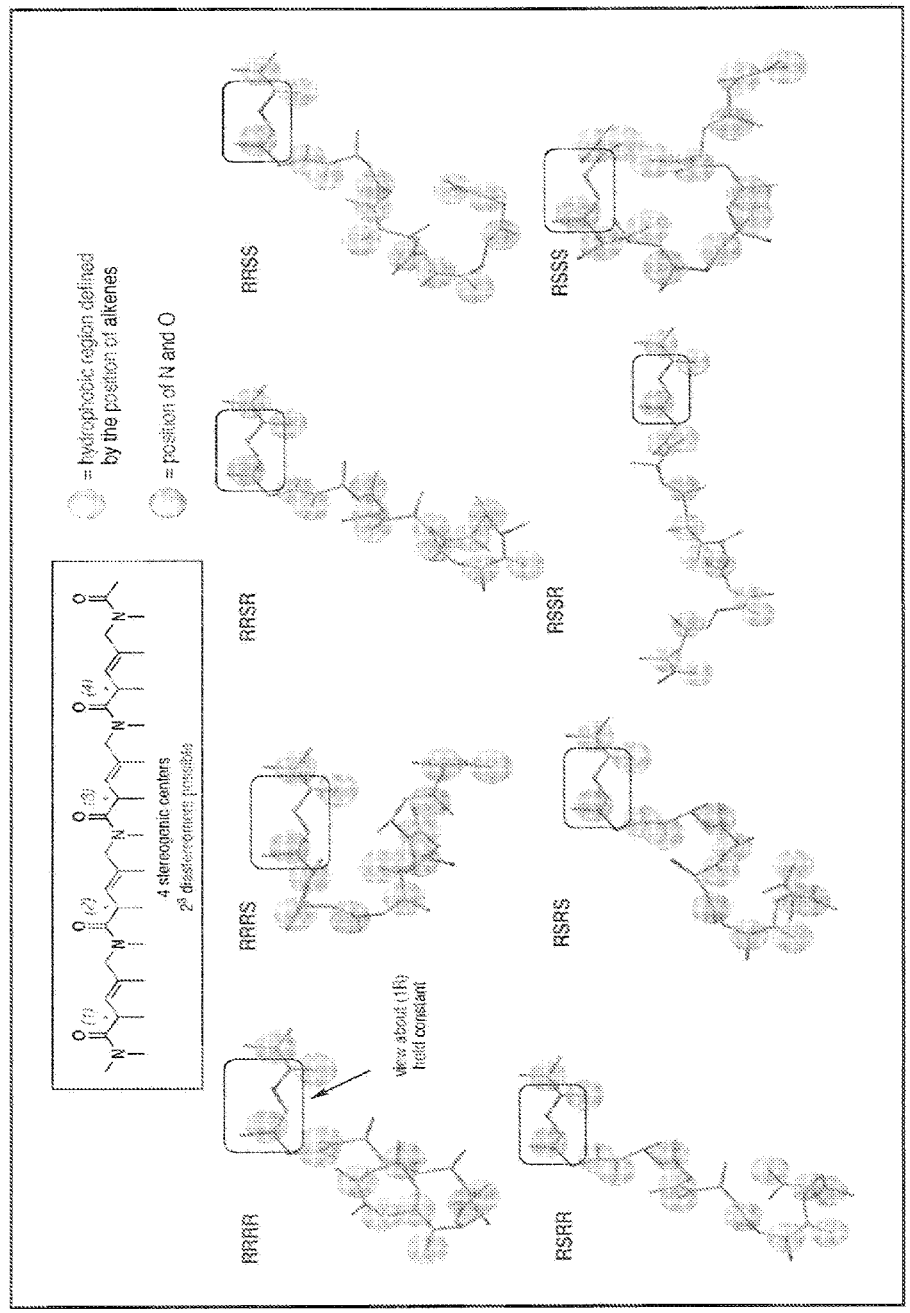
FIG. 2: Stereochemistry of COPA backbone has a substantial impact on skeletal shape and the disposition of side chains in space. Low energy conformations of a collection of eight N-Me substituted isomeric COPA tetramers (MMFF calculations—extracted from a conformer distribution generated in Spartan-08). While fixing the relative position of the C-terminus (boxed within the 3D-models), each diastereomer is depicted in its predicted low energy conformation with colored spheres that highlight the relative position of heteroatoms (green) and alkenes (blue). Not easily depicted, but even more compelling, is that the conformer distribution about each low energy conformation is substantially restricted. In a head-to-head comparison with a polymethylated peptoid tetramer where >12 conformations can be located within 1.8 kcal/mol of the low energy conformer, by MMFF calculations COPAs are predicted to be substantially more rigid—in most cases, only 1-2 conformations were located within 1.8 kcal of the low energy conformation depicted. While these molecular mechanics calculations are not thought to predict the solution phase structure of these simple tetramers, the calculations provide a uniform mathematical filter to support the unique characteristics associated with this new class of synthetic oligomer.

The combined influence of distinct chiral subunits on the gross conformational preferences for a COPA oligomer is profound, and offers a robust strategy to access diverse chiral skeletons that differentially display building blocks. As illustrated in FIG. 2, analysis of a collection of 8 stereoisomeric but homogeneously substituted COPA tetramers (all methyl substitution) illustrates the striking effect that C2 stereochemistry has on the skeletal structure, and hence three-dimensional orientation of all building blocks to be installed.

Figure 12:
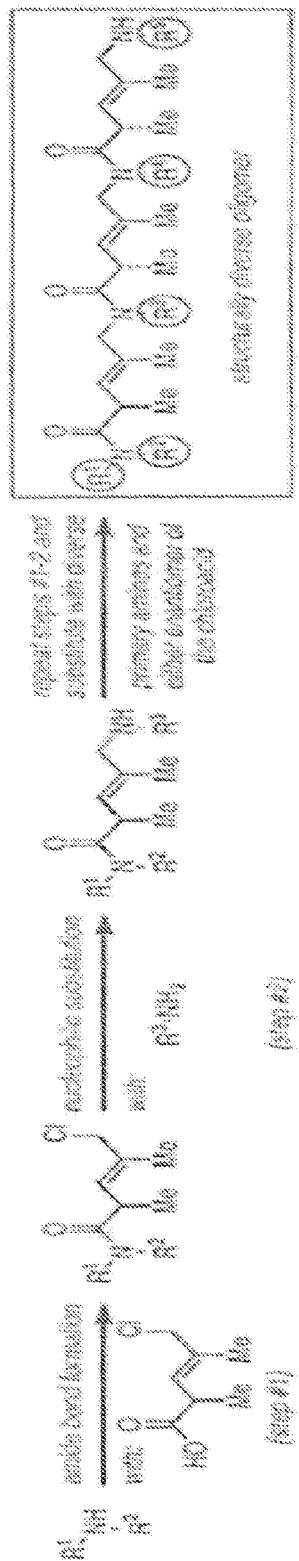
FIG. 12 is a schematic representation showing an example of oligomer synthesis, wherein $R^1$, $R^2$, $R^3$, $R^4$, and $R^5$ independently comprise any functionality that does not interfere with the ability to perform the given chemical homologation defined by: 1) amide bond formation, and 2) nucleophilic substitution (displacement of the allylic chloride). Examples of such functionality include, but is not limited to alkyl, aryl, heteroaryl, $NR^5R^{5'}$, $OR^5$).

The synthesis of compounds from the methods described in the examples section, which follow, are unique and advantageous over any currently available method. While peptoids, peptides, β-peptides and all other known synthetic oligomers can be prepared in great numbers, their skeletons (or core units) are typically not conformationally biased. In some cases, high molecular weight oligomers, or designed oligomers that are rigidified by various macromolecular interactions (i.e. charge separation, π-stacking, hydrogen-bonding, etc.), are needed to achieve conformational rigidity. Having to rely on such features greatly diminishes the potential of such molecular skeletons in diversity-oriented synthesis and ligand discovery due to a constraining of the type of substituents or molecular weight required to achieve rigidification. The advantages of the methods described herein are that they can be employed to prepare chiral oligomers of massive number and molecular diversity while doing so in a manner that rigidifies the core skeleton. The result of this rigidification is a preferential orientation of diversity elements (i.e. $R^1$-$R^7$) in three-dimensional space, about a skeleton of relative low molecular weight (in comparison to proteins and other biological macromolecules). Other advantages include: 1) a very simple method of synthesis which proceeds in high-yields, 2) great diversity in building blocks is readily achieved with available primary amines, 3) compounds are prepared as single enantiomers, 4) compounds are prepared in diastereomerically pure form, and 5) compounds have defined conformational preferences based, in part, by the minimization of non-bonded steric interactions (allylic strain) that results from the substitution and stereochemistry of the building block generalized as Formula I. FIG. 12 is a schematic representation showing an example of oligomer synthesis, wherein $R^1$, $R^2$, $R^3$, $R^4$, and $R^5$ independently comprise any functionality that does not interfere with the ability to perform the given chemical homologation defined by: 1) amide bond formation, and 2) nucleophilic substitution (displacement of the allylic chloride). Examples of such functionality include, but is not limited to alkyl, aryl, heteroaryl, $NR^5R^{5'}$, $OR^5$.

In one embodiment, a method of synthesizing a chiral monomer comprises obtaining an oxazolidinone and reacting via a stereoselective aldol reaction with an α-substituted, α,β-unsaturated aldehyde (i.e. including, but not limited to methacrolein). In the present case, MgBr$_2$-catalyzed aldol reaction proceeds to deliver a stereodefined anti-aldol product (Evans, D. A.; Tedrow, J. S.; Shaw, J. T.; Downey, C. W. Diastereoselective Magnesium Halide-Catalyzed anti-Aldol Reactions of Chiral N-Acyloxazolidinones, *J. Am. Chem. Soc.* 2002, 124, 392-393). The product TMS-ether is converted to a stereodefined allylic halide by a stereoselective halogenation reaction that proceeds with allylic transposition (Ravikumar, P. C.; Yao, L.; Fleming, F. F. Allylic and Allenic Halide Synthesis via NbCl$_5$- and NbBr$_5$-Mediated Alkoxide Rearrangements, *J. Org. Chem.* 2009, 74, 7294-7299). Finally, hydrolysis of the oxazolidinone proceeds to deliver the chiral product defined by Formula I'. Here, X=OH, and Y=Cl.

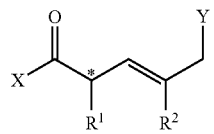

I'

Based on the reactivity of the compound depicted as Formula I' above, the method of synthesis described can be employed to access a range of diverse products related to that described, where X can independently comprise OR$^3$, NR$^4$R$^5$, H, halide, alkyl, alkenyl, cycloalkyl, aryl, heteroaryl, and the like; R$^3$ independently comprises amide, alkyl, cycloalkyl, alkenyl, aryl, heteroaryl, NR$^4$R$^5$, carboxyl, and the like; R$^4$ independently comprises H, OR$^4$, alkyl, aryl, heteroaryl, and the like; *C is a chiral center [(R) or (S)]; R$^1$ independently comprises alkyl, aryl, heteroaryl, alkenyl, OR$^4$, and the like; R$^2$ independently comprises alkyl, cycloalkyl, aryl, heteroaryl, alkynyl, alkenyl, and the like. Y independently comprises a halide, NHR$^4$, NR$^4$R$^5$, OH, OR$^3$, or C(O)X. R$^4$ and R$^5$ are defined by substituents that are compatible with the bond forming reactions required to convert the carboxylic acid-based pentenoic allylic halide to the functionalized product.

In another embodiment, R$^1$ and R$^2$ independently comprise OR$^3$, NHR$^4$, NR$^4$R$^5$, halide, alkyl, linear alkyl, branched alkyl, heteroatom-substituted (i.e. N, O, S, halogen, etc.) alkyl, unsaturated and polyunsaturated linear and branched hydrocarbons, alkenyl, cycloalkyl, aryl, heteroaryl, heteroaryl, heterocycloalkyl, heteroatom-substituted unsaturated and polyunsaturated linear and branched hydrocarbons, cycloalkyl, heteroatom-substituted cycloalkyl, saturated and unsaturated heterocycles, substituted cycloalkyl, substituted and unsubstituted aromatic, substituted and unsubstituted heteroaromatic; R$^3$ independently comprises H, alkyl, cycloalkyl, alkenyl, aryl, heteroaryl, NR$^4$R$^5$, carboxyl, heterocycloalkyl; and, R$^4$ independently comprises H, OR$^3$, alkyl, aryl, or heteroaryl.

The optically active monomers comprising the structure of Formula I' can be employed in oligomerization chemistry as previously discussed (in solution or on a solid phase). The products of such oligomerization can be diverse based on substitution and stereochemistry of the central unsaturated building block and, in some cases, the nature of the amine building block (if displacing the allylic chloride is employed as a key homologation step), as well as the nature of the backbone, which can incorporate carboxylic acid-based building blocks of different substitution (i.e. bromoacetic acid in place of the 2-substituted 3-pentenoic acid monomer depicted as Formula 1' where X=OH, and Y=Cl). Various methods including stereoselective hydrogenation, hydroboration, dihydroxylation, cyclopropanation, epoxidation and aziridination may be employed to mutate the core skeleton inherent to Formula 1' to stereodefined motifs that lack the central alkene.

Examples of novel compounds of Formula I' which can be synthesized are shown below. This is not an exhaustive list nor meant to limit the invention.

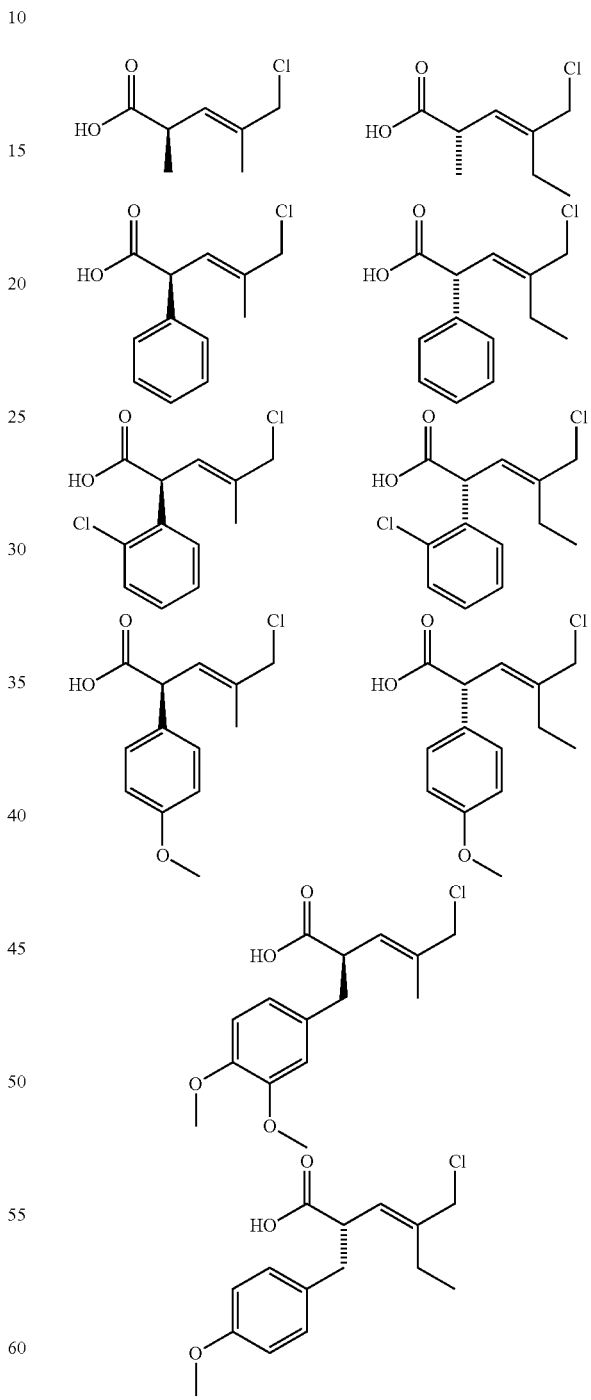

As an example and not wishing to be bound or limited to any particular substitutions of compounds of Formula I' as any type of molecule known or yet to be discovered can be used, such as, for example, R$^1$ comprises alkyl, substituted and unsubstituted aryl, as well as substituted hydrocinnammyl. $R^2$ comprises alkyl (Me vs. Et).

Without wishing to be bound by theory, molecules of general Formula I' are comprised of a chiral halopentenoic acid backbone, where the nature and stereochemistry of this core influence the relative three dimensional orientation of substituents $R^1$ and $R^2$ that extend from this backbone. The precise nature of substituents $R^1$ and $R^2$ is broad, includes both known and yet to be discovered molecules and comprise molecular features that provide a desired therapeutic, diagnostic, or physical property. Examples within the scope of this invention include: linear alkyl, branched alkyl, heteroatom-substituted (i.e. N, O, S, halogen, etc.) alkyl, unsaturated and polyunsaturated linear and branched hydrocarbons, heteroatom-substituted (i.e. N, O, S, halogen, etc.) unsaturated and polyunsaturated linear and branched hydrocarbons, cycloalkyl, heteroatom-substituted cycloalkyl (i.e. saturated and unsaturated heterocycles), substituted cycloalkyl, substituted and unsubstituted aromatic, and substituted and unsubstituted heteroaromatic. This general description of $R^1$ and $R^2$ includes all such molecular architecture, that can be derived from the method of synthesis or, without being bound by theory, motifs that can be introduced after completion of a smaller molecular weight variant of Formula I'.

In some embodiments, a compound of Formula I comprises:

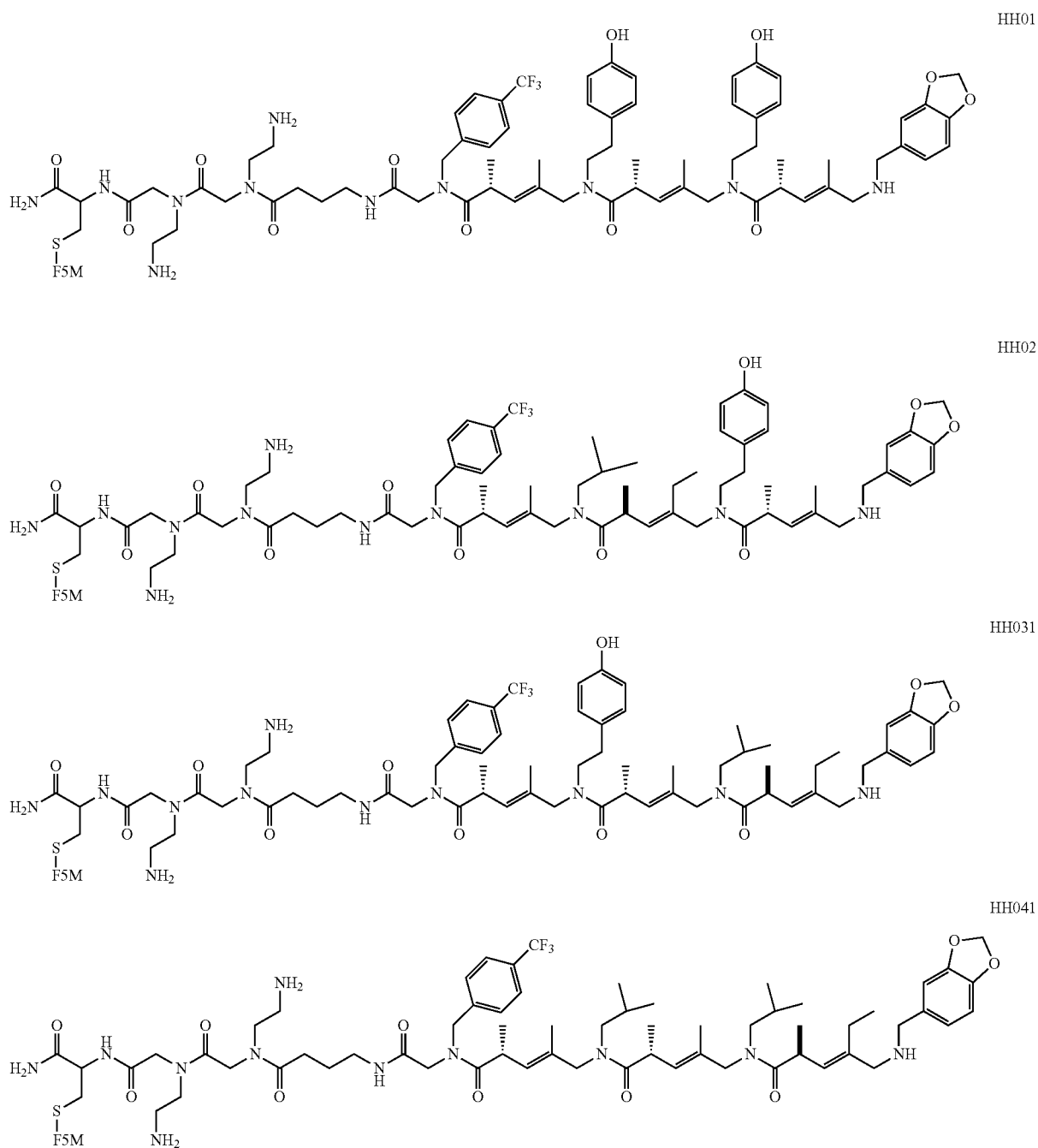

-continued
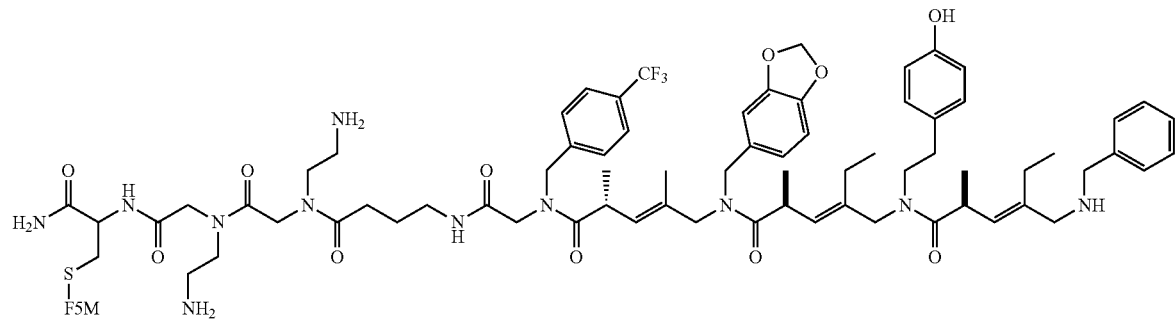
HH05
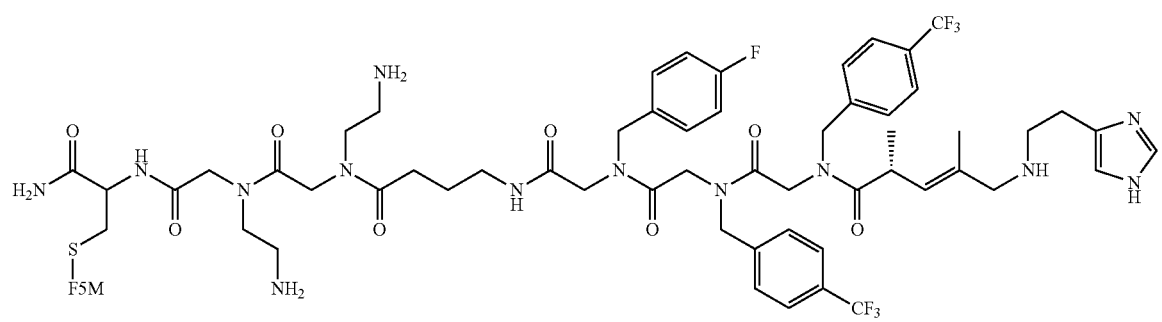
H0442
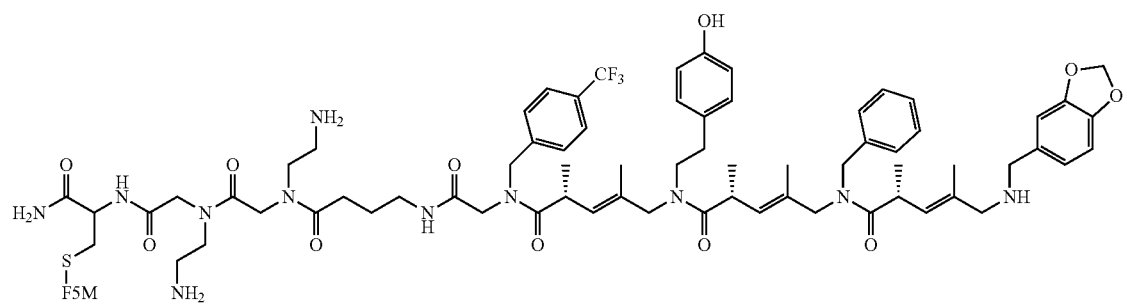
H0610-01
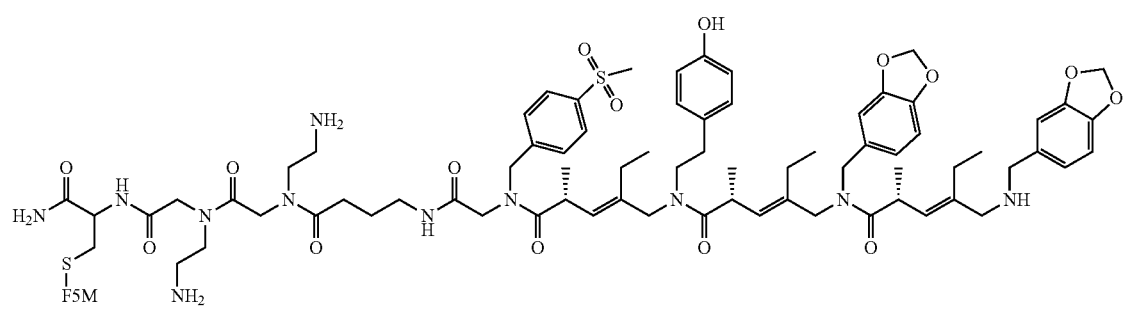
H0610-02
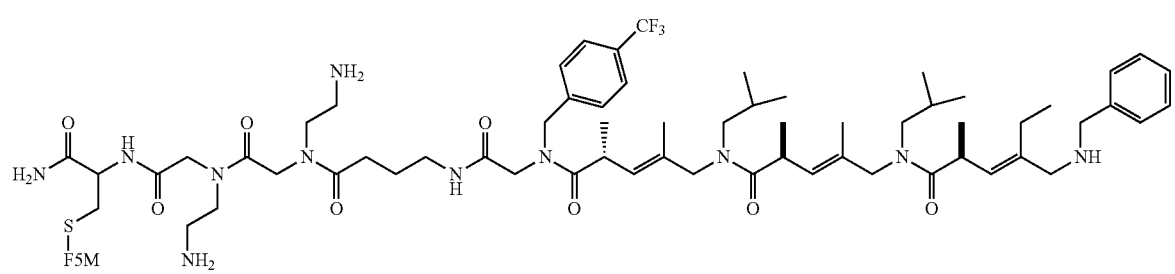
HH06

-continued
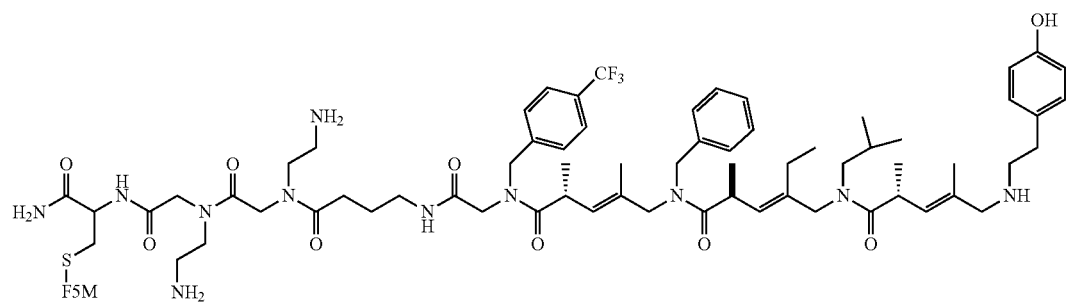
HH07
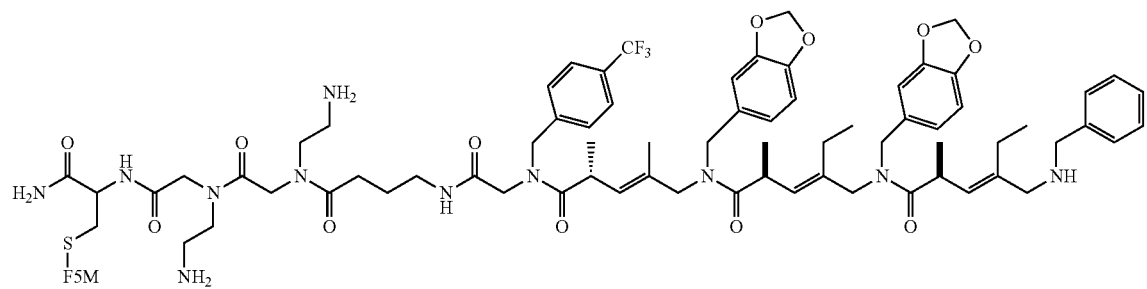
HH08
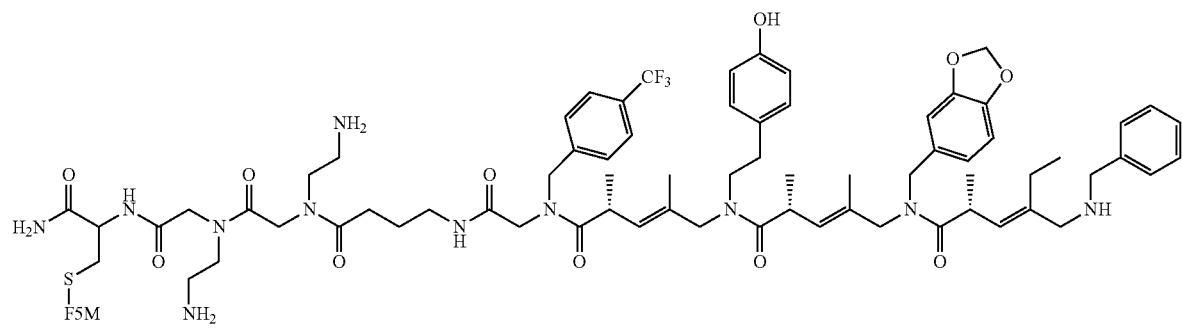
HH09
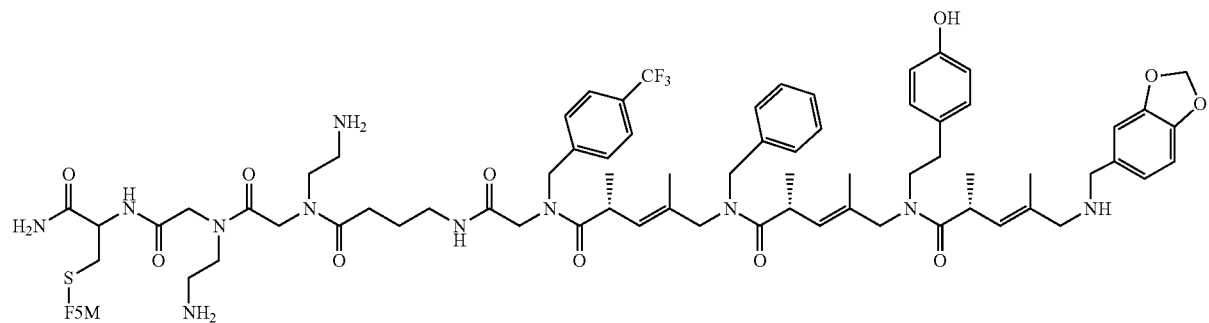
HH10

H0478

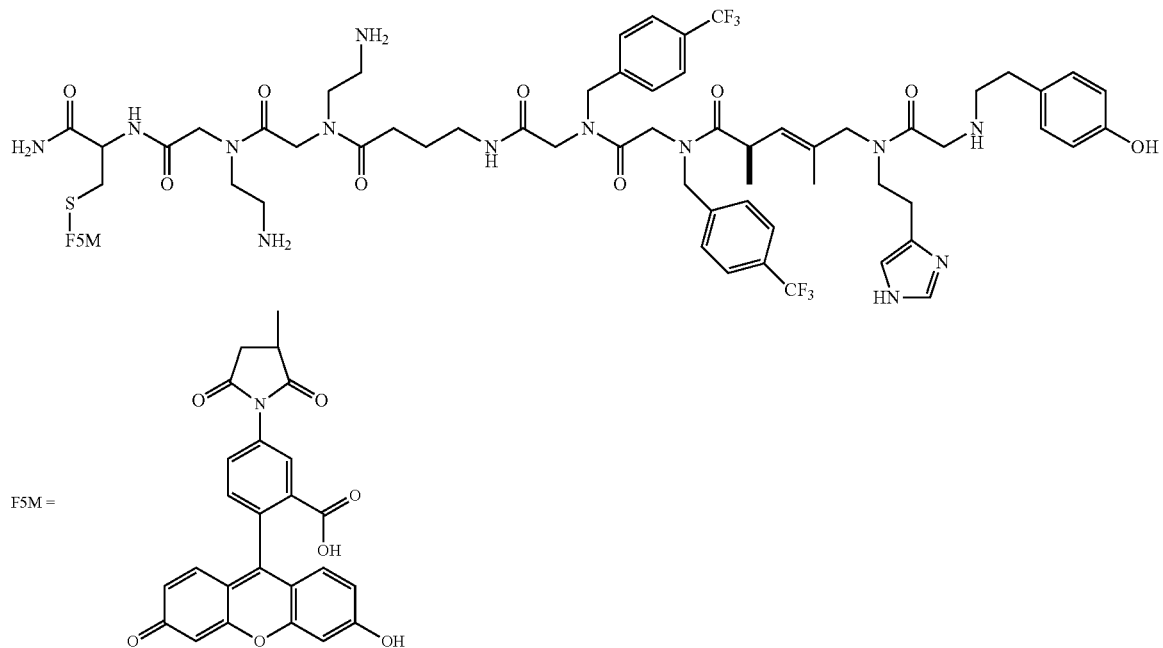

Pharmaceuticals for Diseases or Associated Disorders Thereof.

In embodiments, the compounds can be used to diagnose and treat diseases or disorders associated with an immune system disorder wherein the compounds bind to, for example, immune cell receptors or ligands. Examples of such diseases or disorders include without limitation, hematological malignancies and other cancers, autoimmune diseases, diseases associated with inflammation, transplantation rejection, allergies, neurological diseases or disorders, infections, immune cell mediated diseases or disorders, or combinations thereof.

In one preferred embodiment, a pharmaceutical composition comprises one or more compounds of Formula I conjugated to one or more toxic agents, wherein the conjugate specifically binds to hematopoietic malignant cells. Hematopoietic malignancies include: chronic lymphocytic leukemia (CLL), chronic myeloproliferative diseases, myelodysplastic/myeloproliferative diseases, myelodysplastic syndromes, acute myeloid leukemias, B cell neoplasms, T-cell and NK-cell neoplasms, Hodgkin's lymphoma, histiocytic and dendritic cell neoplasms, mastocytosis and the like.

Examples of histiocytic and dendritic cell neoplasms include, without limitation: macrophage/histiocytic neoplasm, histiocytic sarcoma, dendritic cell neoplasms, Langerhan's cell histiocytosis, Langerhan's cell sarcoma, interdigitating dendritic cell sarcoma/tumor, follicular dendritic cell sarcoma/tumor, dendritic cell sarcoma and the like.

Examples of chronic myeloproliferative diseases include, without limitation: chronic myelogenous leukemia, chronic neutrophilic leukemia, chronic eosinophilic leukemia/hypereosinophilic syndrome, polycythemia, chronic idiopathic myelofibrosis, thrombocythemia, and the like.

Examples of myelodysplastic/myeloproliferative diseases include, without limitation: chronic myelomonocytic leukemia, atypical chronic myelogenous leukemia, juvenile myelomonocytic leukemia, and the like.

Examples of myeloid leukemias or acute myeloid leukemias include, without limitation: acute myeloid leukemia multilineage dysplasia, acute myelomonocytic leukemia, acute monoblastic and monocytic leukemia, acute erythroid leukemia, acute megakaryoblastic leukemia, acute basophilic leukemia, acute panmyelosis with myelofibrosis, myeloid sarcoma, and the like.

Examples of B cell malignancies or neoplasms include, without limitation: precursor hematopoietic neoplasm, precursor B lymphoblastic leukemia, lymphoma, mature hematopoietic neoplasm, chronic lymphocytic leukemia, small lymphocytic lymphoma, hematopoietic prolymphocytic leukemia, lymphoplamacytic lymphoma, splenic marginal zone lymphoma, hairy cell leukemia, plasma cell myeloma, solitary plasmacytoma of bone, extraosseous plasmacytoma, extranodal marginal zone hematopoietic lymphoma of mucosa-associated lymphoid tissue (MALT-lymphoma), nodal marginal zone hematopoietic lymphoma, follicular lymphoma, mantle cell lymphoma, diffuse large hematopoietic lymphoma, mediastinal (thymic) large cell lymphoma, intravascular large hematopoietic lymphoma, primary effusion lymphoma, Burkitt lymphoma, leukemia, lymphomatoid granulomatosis, post-transplant lymphoproliferative disorder, pleomorphic and the like.

Examples of T cell and NK cell neoplasms, include without limitation: precursor T-cell neoplasms, precursor T lymphoblastic leukemia, lymphoma, blastic NK cell lymphoma, mature T-cell and NK-cell neoplasms, T-cell prolymphocytic leukemia, T-cell large granular lymphocytic leukemia, aggressive NK cell leukemia, adult T-cell leukemia/lymphoma, extranodal NK/T cell lymphoma, nasal type lymphoma, enteropathy type T-cell lymphoma, hepatosplenic T-cell lymphoma, subcutaneous panniculitis-like T-cell lymphoma, mycosis fungoides, Sezary Syndrome, Primary cutaneous anaplastic large cell lymphoma, peripheral T-cell lymphoma, angioimmunoblastic T-cell lymphoma, anaplastic large cell lymphoma, T lymphomatoid papulosis and the like.

Examples of Hodgkin lymphomas include without limitation: nodular lymphocyte predominant Hodgkin lymphoma, classical Hodgkin lymphoma, nodular sclerosis classical Hodgkin lymphoma, lymphocyte-rich classical Hodgkin lymphoma, mixed cellularity classical Hodgkin lymphoma, and the like.

Examples of histiocytic and dendritic cell neoplasms include without limitation: macrophage/histiocytic neoplasm, histiocytic sarcoma, dendritic cell neoplasms, Langerhan's cell histiocytosis, Langerhan's cell sarcoma, interdigitating dendritic cell sarcoma/tumor, follicular dendritic cell sarcoma/tumor, dendritic cell sarcoma, and the like.

Examples of mastocytosis include without limitation: cutaneous mastocytosis, indolent systemic mastocytosis, systemic mastocytosis with associated clonal, hematological non-mast cell lineage disease, aggressive systemic mastocytosis, mast cell leukemia, mast cell sarcoma, extracutaneous mastocytoma and the like.

In preferred embodiments, the hematopoietic malignancy is B cell chronic lymphocytic leukemia (B-CLL). B-CLL is an accumulative disease of slowly proliferating $CD5^+$ B lymphocytes that develops in the aging population. Whereas some patients with B-CLL have an indolent course and die after many years from unrelated causes, others progress very rapidly and succumb within a few years from this currently incurable leukemia. Over the past decade, studies of the structure and function of the B cell antigen receptor (BCR) used by these leukemic cells have helped redefine the nature of this disease.

$CD5^+$ B lymphocytes in B-CLL patients express low levels of surface membrane Ig that serves as their receptor for antigen (BCR). The genetics of this Ig have clinical relevance, as patients with an Ig that is unmutated in the variable (V) regions have a significantly worse outcome than those with significant numbers of mutations in the Ig V region.

There are several lines of evidence supporting a role for the Ig molecule in the evolution of B-CLL. Analysis of V region gene cassette usage has provided inferential evidence that the Ig molecules on B-CLL cells are not the product of random chance. The distribution of variable region gene cassettes used by B-CLL clones differs from that found in normal cells with an increased frequency of certain $V_H$ genes. Furthermore, the distribution of mutations among B-CLL cases using these specific $V_H$ genes is selectively and strikingly biased. For instance, the $V_H$ genes of about 40% of B-CLL cases contain <2% differences from the most similar germline gene and about 25% are identical to a germline $V_H$ counterpart.

More recently, sets of B-CLL cases with highly similar Ig molecules have been identified. Unmutated IgG-expressing B-CLL cases in which the BCR was remarkably similar in structure have been identified. These Ig molecules used the same $V_H$, D, $J_H$, and in all but one instance the same $V_K$-$J_K$. Furthermore, the HCDR3s were highly similar in sequence and the LCDR3s were virtually identical with a $V_K$-$J_K$ junction contained an invariant, non-templated arginine codon. A larger set of patients expressing a $V_{H3-21}$ chain and a Vλ-3H/Jλ3 L chain have been described by Tobin et al.

(*Blood* 101(12):4952-7 (2003); Genes Chromosomes Cancer. 2003 August; 37(4):417-20).

As is known, aggressive forms of B-CLL are correlated with B cells that have relatively few IgV gene mutations and have intercellular expression of ZAP-70, and cell surface expression of CD38 and CD23. These markers are evaluated at first diagnosis to predict which patients will have an aggressive form of the disease, in order to determine a course of treatment. Because the B-CLL cells from patients belonging to identified "sets" with common B cell receptor genes have low or absent IgV mutations (see, the Examples section).

In embodiments, one or more compounds of Formula I specifically bind to B cell receptors of B-CLL's. The compounds can be conjugated to a chemotherapeutic or any other toxic agent providing specific delivery to B-CLL's of the agent. Since the compounds selectively bind to the malignant cells and not normal cells, the associated drawbacks of conventional chemotherapy or radiotherapy are thus avoided.

The uses of these compounds are not limited to the treatment of B-CLL but can be used to treat other cancers. In some embodiments, methods of treating cancer include where the cancer is breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, or villous colon adenoma.

In other embodiments, the disease or disorder to be treated are immune cell mediated, such as for example, autoimmune diseases, transplantation rejection, lymphoproliferative disorders, neuroinflammatory diseases, inflammatory diseases, and related disorders thereof. The inflammatory disease can be systemic and local inflammation, arthritis including rheumatoid arthritis, inflammation related to immune suppression, organ transplant rejection, allergies, ulcerative colitis, Crohn's disease, dermatitis, asthma, systemic lupus erythematosus, Sjogren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis.

An inflammatory or inflammation-related disorder is characterized by a local or systemic, acute or chronic inflammation. Examples include inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), acute respiratory distress syndrome, fulminant hepatitis, pancreatitis, hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), asthma, and allergic rhinitis. Examples also include autoimmune diseases (e.g., rheumatoid arthritis, psoriatic arthritis, systemic lupus erythematosus, myasthenia gravis, juvenile onset diabetes, glomerulonephritis, autoimmune throiditis, ankylosing spondylitis, systemic sclerosis, and multiple sclerosis), acute and chronic inflammatory diseases (e.g., systemic anaphylaxia or hypersensitivity responses, drug allergies, insect sting allergies, allograft rejection, and graft-versus-host disease), Sjogren's syndrome, human immunodeficiency, and virus infection. Examples of lymphoproliferative disorders include without limitation: Hodgkin's disease, non-Hodgkin's lymphoma, Burkitt's lymphoma, myeloma, a monoclonal gammopathy with antibody-mediated neurologic impairment. Examples of autoimmune diseases include systemic lupus erythematosus, myasthenia gravis, Grave's disease, type I diabetes mellitus, autoimmune peripheral neuropathy, and autoimmune hemolytic anemia.

In all embodiments, the compounds embodied herein, conjugated or otherwise can be used in conjunction with conventional therapies. For example: anti-inflammatory agents, chemotherapeutics, immune-suppressive drugs, surgery, radiotherapies and the like. In embodiments, the agent is conjugated to or linked to one or more compounds of Formula I. Examples of agents for linking or conjugation to compounds of Formula I include, without limitation, antibodies, aptamers, peptides, proteins, glycosylated moieties, receptor molecules, ligands, natural or synthetic molecules, organic or inorganic molecules, toxins, chemotherapeutic agents, anti-inflammatory agents, steroids, hormones, enzymes, nucleic acids, anti-sense nucleic acids, and the like. In some embodiments, the compounds of Formula I conjugated to one or more agents are administered to a patient in conjunction with conventional therapies.

The agents conjugated to compounds of Formula I embodied herein, may be any of various therapeutic and diagnostic agents which are desired to be delivered to a target. Therapeutic agents which can be included as agents in the delivery system of the present invention illustratively include but are not limited to therapeutic compounds such as an analgesic, an anesthetic, an antibiotic, an anticonvulsant, an antidepressant, an antimicrobial, an anti-inflammatory, anti-migraine, an antineoplastic, an antiparasitic, an antitumor agent, an antiviral, an anxiolytic, a cytostatic, cytokine, a hypnotic, a metastasis inhibitor, a sedative and a tranquilizer.

In another preferred embodiment, the molecules are labeled with a detectable agent, which are administered to a patient for the in vivo imaging. The specific delivery of the detectable agent provides a vastly superior means of specific detection of a tumor or desired target cell and decreases any background noise, allowing for the early detection and diagnosis of a patient's condition or disease.

A "chemotherapeutic agent" is a chemical compound useful in the treatment of cancer, regardless of mechanism of action. In embodiments, one or more chemotherapeutic agents are conjugated to one or more monomers of compounds of Formula I. In other embodiments, the chemotherapeutic agents are administered in addition to the compounds embodied herein. Classes of chemotherapeutic agents include, but are not limited to: alkylating agents, antimetabolites, spindle poison plant alkaloids, cytotoxic/ antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA™, Genentech/OSI Pharm.), docetaxel (TAXOTERE™, Sanofi-Aventis), 5-FU (fluorouracil, 5-fluorouracil, CAS No. 51-21-8), gemcitabine (GEMZAR™, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL.™, Bristol-Myers Squibb Oncology, Princeton, N.J.), trastuzumab (HERCEPTIN™, Genentech), temozolomide (4-methyl-5-oxo-2,3,4,6,8-pentazabicyclo [4.3.0]nona-2,7,9-triene-9-carbox-amide, CAS No. 85622-93-1, TEMODAR™ TEMODAL™, Schering Plough), tamoxifen ((Z)-2-[4-(1,2-diphenylbut-1-enyl)phenoxy]-N, N-dimethylethanami-ne, NOLVADEX™, ISTUBAL™, VALODEX™), and doxorubicin (ADRIAMYCINO™), Akti-1/2, HPPD, and rapamycin.

More examples of chemotherapeutic agents include: oxaliplatin (ELOXATIN™., Sanofi), bortezomib (VELCADE™, Millennium Pharm.), sutent (SUNITINIBO™, SU11248, Pfizer), letrozole (FEMARA™, Novartis), imatinib mesylate (GLEEVEC™, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX™, AstraZeneca), leucovorin (folinic acid), rapamycin (sirolimus, RAPAMUNE™., Wyeth), lapatinib (TYKERB™., GSK572016, Glaxo Smith Kline), lonafarnib (SARASAR™, SCH 66336, Schering Plough), sorafenib (NEXAVAR™, BAY43-9006, Bayer Labs), gefitinib (IRESSA™, AstraZeneca), irinotecan (CAMPTOSAR™, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA™, AstraZeneca), chloranmbucil, AG1478, AG1571 (SU 5271; Sugen), temsirolimus (TORISEL™, Wyeth), pazopanib (GlaxoSmithKline), canfosfamide (TELCYTA™, Telik), thiotepa and cyclosphosphamide (CYTOXAN™, NEOSAR™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammalI, calicheamicin omegaIl (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine; novantrone; teniposide; edatrexate; daunomycin; aminopterin; capecitabine (XELODA™ Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX™; tamoxifen citrate), raloxifene, droloxifene, 4-hydroxytamoxifen, trioxifene, keoxifene, LY117018, onapristone, and FARESTON™ (toremifine citrate); (ii) aromatase inhibitors that inhibit the enzyme aromatase, which regulates estrogen production in the adrenal glands, such as, for example, 4(5)-imidazoles, aminoglutethimide, MEGASE™ (megestrol acetate), AROMASIN™ (exemestane; Pfizer), formestanie, fadrozole, RIVISOR™ (vorozole), FEMARA™ (letrozole; Novartis), and ARIMIDEX.™ (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE™, Genta Inc.); (vii) ribozymes such as VEGF expression inhibitors (e.g., ANGIOZYME™) and HER2 expression inhibitors; (viii) vaccines such as gene therapy vaccines, for example, ALLOVECTIN™, LEUVECTIN™, and VAXID™; PROLEUKIN™ rIL-2; topoisomerase 1 inhibitors such as LURTOTECAN™; ABARELIX™ rmRH; (ix) anti-angiogenic agents such as bevacizumab (AVASTIN™, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN™, Genentech); cetuximab (ERBITUX™, Imclone); panitumumab (VECTIBIX™, Amgen), rituximab (RITUXAN.™, Genentech/Biogen Idec), pertuzumab (OMNITARG™, 2C4, Genentech), trastuzumab (HERCEPTIN™, Genentech), tositumomab (Bexxar, Corixia), and the antibody drug conjugate, gemtuzumab ozogamicin (MYLOTARG™, Wyeth).

Anti-inflammatory agents include NSAID agents. The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

In one embodiment, the compounds of Formula I are linked to ligands which comprise: polypeptides such as antibodies or antibody fragments bearing epitope recognition sites, such as Fab, Fab', $F(ab')_2$ fragments, Fv fragments, single chain antibodies, antibody mimetics (such as DARPins, affibody molecules, affilins, affitins, anticalins, avimers, fynomers, Kunitz domain peptides and monobodies), peptoids, aptamers and the like. In one embodiment the first and second ligands are the same type of molecule. In another embodiment, the first and second ligands are different types of molecules. In some embodiments, the first or second ligands comprise: antibodies, antibody fragments, Fv fragments; single chain Fv (scFv) fragments; Fab' fragments; F(ab')2 fragments, humanized antibodies and antibody fragments; camelized antibodies and antibody fragments, human antibodies and antibody fragments, monospecific or bispecific antibodies, disulfide stabilized Fv fragments, scFv tandems ((scFv) fragments), diabodies, tribodies or tetrabodies, peptoids, peptide or nucleic acid aptamers, antibody mimetics or combinations thereof. In other embodiments, the first and second ligands comprise: a polypeptide, antibodies, antibody fragments, antibody mimetics, single chain antibodies, nucleic acids, an aptamer, a peptoid or a sugar moiety or combinations thereof. In certain embodiments, the first and second ligands are peptide or nucleic acid aptamers. In other embodiments, the first and second ligands are sugar moieties comprising glycosaminoglycans, heparan sulfates or chondroitin sulfates.

Other Uses:

The synthesized compounds, preferably, oligomers of the compounds have a multitude of other uses. The methods embodied herein provide for the synthesis of a plurality of compounds via steps which do not require expensive equipment or consumables, they do not require large laboratory spaces or staff, the steps are efficient in producing high yields of compounds and do not require expensive starting materials. The end user has the luxury of designing the compounds in which to build a library so as to assay for any diagnostic application(s), identification of patients at risk of developing a condition or disorder, or any therapeutic effects the synthesized compounds may have. As discussed above, a library of compounds can be designed to have any desired and varying degrees of rigidity or flexibility to produce a desired library. For example, the compounds may comprise R and/or S configuration chirality and combinations thereof. The compounds can then be screened in any type of screening assay, for example, high-throughput screens.

The compounds can be tested for various effects. For example, in the case a therapeutic agent is identified as a candidate for treating cancer, for example, the candidate agent modulates a tumor gene, follow on tests such as, effects of the candidate agent on tumor cells and tissues, gene expression, receptor expression, arresting of cell growth, tumor growth factors and the like.

In other embodiments, the compounds can be used in the synthesis of other compounds, for example, the oligomers can be used as a rigid backbone, and some of the compounds can be used as intermediates or starting materials, and the like.

In other embodiments, the ligands are linked to a detectable label (detectable molecule), either directly or linked via a suitable linker. The present invention is not limited to any particular linker group. Indeed, a variety of linker groups are contemplated, suitable linkers could comprise, but are not limited to, alkyl groups, ether, polyether, alkyl amide linker, a peptide linker, a polypeptide linker, a modified peptide or polypeptide linker, a peptide nucleic acid (PNA) a Poly (ethylene glycol) (PEG) linker, a streptavidin-biotin or avidin-biotin linker, polyaminoacids (e.g. polylysine), functionalized PEG, polysaccharides, glycosaminoglycans, dendritic polymers PEG-chelant polymers, oligonucleotide linker, phospholipid derivatives, alkenyl chains, alkynyl chains, disulfide, or a combination thereof.

In another embodiment, the detectable label is linked to the ligand, through a chemical bond, or noncovalently, through ionic, van der Waals, electrostatic, or hydrogen bonds.

Fluorophores include any compound, composition or molecule capable of emitting light in response to irradiation. In many instances, fluorophores emit light in the visible region of the spectrum. In other instances, the fluorophores can emit light in the non-visible regions of the spectrum, such as ultraviolet, near-ultraviolet, near-infrared, and infrared. For example and without limitation, examples of fluorophores include: quantum dots; nanoparticles; fluorescent proteins, such as green fluorescent protein and yellow fluorescent protein; heme-based proteins or derivatives thereof; carbocyanine-based chromophores, such as IRDye 800CW, Cy 3, and Cy 5; coumarin-based chromophores, such as (7-diethylamino-3-(4'-maleimidylphenyl)-4-methylcoumarin) (CPM); fluorine-based chromophores, such as fluorescein, fluorescein isothiocyanate (FITC); and numerous ALEXA FLUOR™ chromophores and ALEXA FLUOR™ bioconjugates, which absorb in the visible and near-infrared spectra. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners).

Chemiluminescent moieties include any compound, composition or molecule capable of emitting light in response to a chemical reaction. A bioluminescent compound refers to a naturally occurring form of a chemiluminescent compound. Examples of chemiluminescent compounds include: lucigenin, luminol. Examples of bioluminescent compounds include: luciferins, coelenterazines. The emission from chemiluminescent compounds can be detected by luminometers or scanning spectrometers.

The labeled compounds can be used as diagnostics for both in vivo and in vitro use. For example, a compound may be identified as a ligand for a certain receptor which may be up-regulated in a disease state (e.g. tumor antigens). The compounds can be labeled with a detectable label in order to detect binding.

In another preferred embodiment, a candidate compound has a direct therapeutic effect, that is, without the requirement of any other modifications. The identified compounds can be then used in the prevention or treatment of that disease or disorder. For example, treatment of: inflammatory disease, neuroinflammatory diseases, cancer, neurological diseases, cardiovascular diseases, parasitic or bacterial diseases, viral diseases, central nervous system diseases, brain diseases, etc.

In some embodiments, the methods are used to identify and quantify a specific molecule in a sample, for example, for diagnostic purposes, or monitoring the response to treatment or metabolism of drugs in vivo, etc. In some embodiments, a method of quantifying a specific molecule, e.g. a protein in a sample, the method comprises the steps of: placing the sample containing the specific target molecule into a receptacle, contacting the sample with one or more compounds of Formula I wherein the compounds are conjugated to a detectable label and quantifying the target molecule. The Examples section details the steps of the types of assays employed.

In some embodiments, a method of quantifying a specific molecule, e.g. a protein in a sample, the method comprises a Förster Resonance Energy Transfer (FRET), Bioluminescence Resonance Energy Transfer (BRET), or fluorescence polarization assay.

In one embodiment, the assay employs Förster Resonance Energy Transfer or FRET, a process in which a fluorophore ("donor") that can be excited by light and can transfer the excitation to a second fluorophore ("acceptor") if and only if they are sufficiently close, that is, within a distance in the order of 100 Å or less, defined by the Förster radius. Although FRET is used as an illustrative example, the assays are not limited to FRET based assays. For example, an assay which uses a bioluminescent protein, such as luciferase, to excite a proximal fluorophore (BRET), typically a fluorescent protein (Xu et al. (1999) *Proc. Natl. Acad. Sci. USA* 96(1), 151-6). Another assay alternative is a luminescent oxygen-channeling chemistry (Ullman et al. (1994) *Proc. Natl. Acad. Sci. USA* 91(12), 5426-30), wherein a light induced singlet oxygen generating system transfers the singlet oxygen to a chemiluminescent system in proximity.

In one embodiment, the donor and acceptor fluorophores (detectable label/detectable molecules) are attached to two distinct compounds of Formula I, for example, varying oligomers of Formula I that can bind specifically to distinct sites of one and the same target, for example, B-CLL. When the compounds carrying the donor and the acceptor fluorophore, respectively, bind to the same target molecule and in doing so become sufficiently close to each other, irradiation of the sample at a wavelength that allows excitation of the donor results in emission of radiation by the acceptor. Compounds that are not bound to the same target do not give rise to FRET and therefore need not be removed prior to measurement of emitted radiation.

In other embodiments, the assay is an immunoassay. For example, ELISA's RIA's, Western blots, gels, immunoblots, and the like. In other examples, the assays, comprise nucleic acid based assays (e.g. hybridization assays). In embodiments, the assays are high-throughput screening assays.

In embodiments, the target is present in a sample comprising: a liquid, a semi-liquid, a gel, a biological sample, an intact cell, a permeabilized cell, a disrupted cell, a cell homogenate, a membrane, or a cellular organelle.

Pharmaceutical Compositions

The pharmaceutical compositions of the invention may contain, for example, more than one specificity. In some examples, a pharmaceutical composition of the invention, containing one or more compounds of the invention, is administered in combination with another useful composition such as an anti-inflammatory agent, an immunostimulator, a chemotherapeutic agent, an antiviral agent, or the like. Furthermore, the compositions of the invention may be administered in combination with a cytotoxic, cytostatic, or chemotherapeutic agent such as an alkylating agent, antimetabolite, mitotic inhibitor or cytotoxic antibiotic, as described above. In general, the currently available dosage forms of the known therapeutic agents for use in such combinations will be suitable.

Combination therapy (or "co-therapy") includes the administration of a compound of Formula I, Formula I conjugated to one or more agents that are administered with a second agent as part of a specific treatment regimen intended to provide the beneficial effect from the co-action of these therapeutic agents. In addition, some compounds of Formula I may be conjugated to one agent and other compounds of Formula I are conjugated to another agent and are administered as part of the combination therapy. The beneficial effect of the combination includes, but is not limited to, pharmacokinetic or pharmacodynamic co-action resulting from the combination of the compounds embodied herein and therapeutic agents. Administration of these the compounds embodied herein and therapeutic agents in combination typically is carried out over a defined time period (usually minutes, hours, days or weeks depending upon the combination selected).

Combination therapy may, but generally is not, intended to encompass the administration of two or more of these compounds embodied herein and therapeutic agents as part of separate monotherapy regimens that incidentally and arbitrarily result in the combinations of the present invention. Combination therapy is intended to embrace administration of these therapeutic compounds embodied herein, in a sequential manner, that is, wherein each the compounds embodied herein and therapeutic agent are administered at a different time, as well as administration of the compounds embodied herein and therapeutic agents, or at least two of the compounds embodied herein and, in a substantially simultaneous manner. Substantially simultaneous administration can be accomplished, for example, by administering to the subject a single capsule having a fixed ratio of each of the compounds embodied herein and therapeutic agent or in multiple, single capsules for each of the compounds embodied herein and/or therapeutic agents.

Sequential or substantially simultaneous administration of each of the compounds embodied herein and therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the compounds embodied herein and therapeutic agents are administered is not narrowly critical unless noted otherwise. Combination therapy also can embrace the administration of the compounds embodied herein and therapeutic agents as described above in further combination with other biologically active ingredients. Where the combination therapy further comprises a non-drug treatment, the non-drug treatment may be conducted at any suitable time so long as a beneficial effect from the co-action of the combination of the compounds embodied herein and the therapeutic agents and non-drug treatment is achieved. For example, in appropriate cases, the beneficial effect is still achieved when the non-drug treatment is temporally removed from the administration of the compounds embodied herein and therapeutic agents, perhaps by days or even weeks.

Therapeutic or pharmacological compositions of the present invention will generally comprise an effective amount of the active component(s) of the therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

For any compound used in the methods of the invention, the therapeutically effective amount or dose can be estimated initially from activity assays in cell cultures and/or animals. For example, a dose can be formulated in animal models to achieve a circulating concentration range that includes the $IC_{50}$ as determined by activity assays (e.g., the concentration of the test compound, which achieves a half-maximal inhibition of the proliferation activity). Such information can be used to more accurately determine useful doses in humans.

Toxicity and therapeutic efficacy of the compounds described herein can be determined by standard pharmaceutical procedures in experimental animals, e.g., by determining the $IC_{50}$ and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1). Dosage amount and interval may be adjusted individually to provide plasma levels of the active moiety which are sufficient to maintain therapeutic effects, termed the minimal effective concentration (MEC). The MEC will vary for each preparation, but can be estimated from in vitro and/or in vivo data, e.g., the concentration necessary to achieve 50-90% inhibition of a proliferation of certain cells may be ascertained using the assays described herein. Dosages necessary to achieve the MEC will depend on individual characteristics and route of administration. HPLC assays or bioassays can be used to determine plasma concentrations. Dosage intervals can also be determined using the MEC value. Preparations should be administered using a regimen, which maintains plasma levels above the MEC for 10-90% of the time, preferable between 30-90% and most preferably 50-90%. Depending on the severity and responsiveness of the condition to be treated, dosing can also be a single administration of a slow release composition described hereinabove, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, etc.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or other known methods.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

The pharmaceutical compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

Effective doses of the compositions of the present invention, for the treatment of the above described diseases, vary depending upon may different factors, including means of administration, physiological state of the patient, whether the patient is human or an animal, other medications administered, and whether treatment is prophylactic or therapeutic. Usually, the patient is a human, but in certain embodiments, a patient is an animal, particularly an animal selected from a mammalian species including rat, rabbit, bovine, ovine, porcine, canine, feline, murine, equine, and primate.

The compounds can be administered on multiple occasions, wherein intervals between single dosages can be daily, weekly, monthly, or yearly. Alternatively, one or more of the compounds of the invention can be administered as a sustained-release formulation, in which case less frequent administration is required. Dosage and frequency may vary depending on the half-life of the compounds of the invention. In therapeutic applications, a relatively high dosage at relatively short intervals is sometimes required until progression of the disease is reduced or terminated, and sometimes until the patient shows partial or complete amelioration of symptoms of the disease. Thereafter, the patient can be administered a prophylactic regime.

Administration of a pharmaceutical composition of the compounds described herein can be carried out via a variety of routes including, but are not limited to, oral, topical, pulmonary, rectal, subcutaneous, intradermal, intranasal, intracranial, intramuscular, intraocular, or intra-articular injection and the like. One or more compounds described herein can optionally be administered in combination with other biological or chemical agents that are at least partly effective in treatment of a disease.

As noted above, the compounds described herein may be administered for example, but are not limited to, orally, topically, pulmonary, rectally, subcutaneously, intradermally, intranasally, intracranially, intramuscularly, intraocularly, or intra-arterially and the like. The carrier or excipient or excipient mixture can be a solvent or a dispersive medium containing for example, but are not limited to, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Moreover, other or supplementary active ingredients can also be incorporated into the final composition.

Administration of the compounds embodied herein, by intravenous formulation is well known in the pharmaceutical industry. An intravenous formulation should possess certain qualities aside from being just a composition in which the compounds embodied herein are soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of compounds of the present invention as follow: solvents: ethanol, glycerol, propylene glycol; stabilizers: ethylene diamine tetraacetic acid (EDTA), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer may be necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/ disodium hydrogen phosphate.

The compositions can be formulated in an oral unit dosage form. The term "unit dosage forms" refers to physically discrete units suitable as unitary dosages for a patient, each unit containing a predetermined quantity of active material calculated to produce the desired therapeutic effect, in association with a suitable pharmaceutical excipient.

Kits and Methods

The present invention further provides systems and kits (e.g., commercial therapeutic, diagnostic, or research products, reaction mixtures, etc.) that contain one or more or all components sufficient, necessary, or useful to practice any of the methods described herein. These systems and kits may include buffers, detection/imaging components, positive/ negative control reagents, instructions, software, hardware, packaging, or other desired components.

The kits provide useful tools for diagnosis, treatment of patients, screening of compounds for therapeutic potential and the like, and contain one or more compounds of Formula I. In some embodiments, the kits comprise the compounds of Formula I and one or more detectable labels or therapeutic agents. In other embodiments, the kits comprise the compounds of Formula I conjugated to linked to one or more detectable labels or therapeutic agents. The kits can be packaged in any suitable manner to aid research, clinical, and testing labs, typically with the various parts, in a suitable container along with instructions for use.

In certain embodiments, the kits may further comprise, where necessary, agents for reducing the background interference in a test, positive and negative control reagents, apparatus for conducting a test, and the like.

In certain embodiments of the methods and kits provided herein, solid phase supports are used for purifying proteins, labeling samples or carrying out the solid phase assays. Examples of solid phases suitable for carrying out the methods disclosed herein include beads, particles, colloids, single surfaces, tubes, multiwell plates, microtiter plates, slides, membranes, gels and electrodes. When the solid phase is a particulate material (e.g., beads), it is, in one embodiment, distributed in the wells of multi-well plates to allow for parallel processing of the solid phase supports.

Methods and kits disclosed herein may be carried out in numerous formats known in the art. In certain embodiments, the methods provided herein are carried out using solid-phase assay formats. In certain embodiments, the methods provided herein are carried out in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (e.g., round- or flat-bottom multi-well plates). Exemplary multi-well plate formats that can be used in the methods provided herein include those found on 96-well plates (12×8 array of wells), 384-well plates (24×16 array of wells), 1536-well plate (48×32 array of well), 3456-well plates and 9600-well plates. Other formats that may be used in the methods provided herein include, but are not limited to, single or multi-well plates comprising a plurality of domains, cuvettes, microarrays etc. In certain embodiments, the plates are black-wall, black-bottom plates. In certain embodiments, the plates are black-wall, white-bottom plates. In certain embodiments, the plates have black walls and clear bottoms in order to allow bottom reading of the fluorescence signals. In certain embodiments, the plates are chosen with minimal and uniform intrinsic fluorescence intensity within the range utilized in the method to avoid interference with the FRET signals.

The methods provided herein, when carried out in standardized plate formats can take advantage of readily available equipment for storing and moving these plates as well as readily available equipment for rapidly dispensing liquids in and out of the plates (e.g., robotic dispenser, multi-well and multi-channel pipettes, plate washers and the like).

The invention has been described in detail with reference to preferred embodiments thereof. However, it will be appreciated that those skilled in the art, upon consideration of this disclosure, may make modifications and improvements within the spirit and scope of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

While various embodiments of the present invention have been described above, it should be understood that they have been presented by way of example only, and not limitation. The following non-limiting examples are illustrative of the invention.

Figures 3A, 3B, 3C, 3D, 3E, 3F:
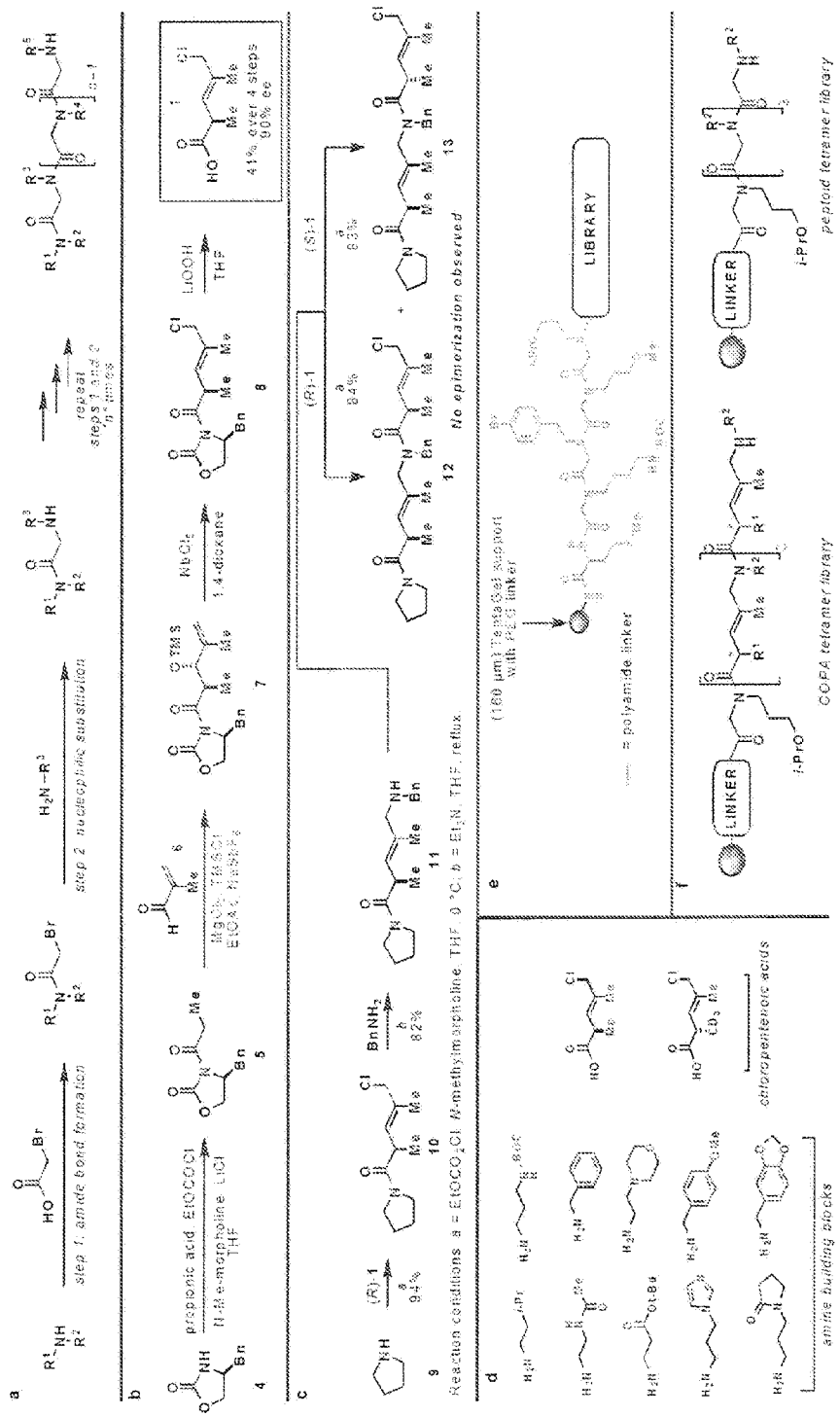
FIGS. 3A-3F are a schematic representation showing the chemical development of COPA oligomers: From general oligomerization strategy, asymmetric synthesis and library construction.

Example 1: A Biomimetic and Polyketide-Inspired Approach to Small Molecule Ligand Discovery Development of Approach:

Synthetically, COPAs have been designed to be accessible using a "sub-monomer" route akin to that employed in peptoid synthesis (FIG. 3A). This would allow simple primary amines, of which hundreds are commercially available, to be employed as one of the diversity elements in split-and-pool library synthesis. Furthermore, this design was optimistically thought to be compatible with MS-MS analysis, where the compound derived from a single bead would be sufficient to decode the precise structure of oligomer present. As such, one could avoid employing an encoding strategy to elucidate hit-structure.

To affect this strategy, a practical and scalable synthesis of both antipodes of chloropentenoic acids like 1 was required (see, FIG. 3B). Ideally, this synthesis would also be capable of delivering future analogs of 1 with diverse C2 and C4 substitution. Therefore, a convergent synthetic pathway was targeted to facilitate future analog generation that could avoid chromatographic purification at any step, and that would proceed from readily available starting materials, limit the use of air and moisture sensitive reagents, and deliver the chiral monomers with high levels of stereochemical fidelity. The solution to this problem is depicted in FIG. 3B.

Results:

Synthesis of the propionyl oxazolidinone 4 was accomplished without the requirement of a highly reactive base (Ho, G-J et al. *J. Org. Chem.* 60, 2271-2273 (1995)) and subsequent stereoselective aldol reaction with methacrolein (Nielsen, P. E. *Chem. Biodivers.* 7, 786-804 (2010)) was achieved under reaction conditions that do not require pre-generation of a metal enolate (Evans, D. A et al. *J. Am. Chem. Soc.* 124, 392-393 (2002)). Isolated by simple extraction, the TMS-ether 7 was converted to the stereodefined allylic chloride 8 by Nb-mediated stereoselective halogenation (E:Z≥20:1) (Ravikumar, P. C. et al. *J. Org. Chem.* 74, 7294-7299 (2009)). While seemingly difficult to accomplish in a highly selective fashion, hydrolysis of the imide proceeded uneventfully (without significant hydrolysis of the allylic chloride) and delivered 1 in ≥95% ee and 41% overall yield. Notably, this synthesis procedure delivers optically active 1 in acceptable yield and purity through a four-step sequence that does not require a single chromatographic operation. As an indication of the robust nature of this sequence, 10 g of 4 was converted to ca. 4 g of 1 routinely.

As depicted in FIG. 3B, solution phase amide bond formation with a simple secondary amine (via the mixed anhydride) proceeded effectively, in this case delivering the chloroamide 10 in 94% yield. Unlike related coupling reactions for the synthesis of peptides, no evidence was found for epimerization of the potentially labile α-stereocenter of 10. Subsequent coupling with benzylamine proceeded in a similarly straightforward manner, delivering aminoamide 11 in 82% yield. This two-step sequence validates the central steps of the proposed oligomerization of 1 and confirms that chiral chloroacids of this and related structures can be functionalized in a manner related to α-bromoacetic acid in peptoid synthesis.

Subsequent homologation of 11 with either enantiomer of 1 leads to the production of the corresponding dimers 12 and 13 with similarly high levels of efficiency, indicating that double asymmetric relationships between amine 11 and acid 1 have little impact on chemical efficiency for this bond construction.

Moving forward to explore the utility of COPA oligomers as a potential source of protein ligands, a library of tetramers was prepared by split-and-pool methods. To be compatible with the on-bead screening platform (Xiao, X et al. *J. Comb. Chem.* 9, 592-600 (2007)), 160 μm TENTAGEL beads were selected, that were functionalized with a tetrameric polyamide (FIG. 3D). Targeting a library of 160,000 members, ten primary amines and two pentenoic acids were employed, as depicted in FIG. 3E. Since structural elucidation was to be conducted by mass spectrometry, a heavy atom label ($CD_3$ at C2) was employed to correlate differences in the mass of fragment ions with absolute stereochemistry at that center. Alongside these efforts, a library of peptoid tetramers was prepared with the same amines used for the COPA library (FIG. 3E) in an effort to establish a baseline for comparison between these two synthetic oligomer platforms. MALDI mass spectra revealed a single strong peak for the COPAs released from several individual beads chosen randomly from the library, indicating that each bead displays predominantly a single compound and that each synthetic step proceeded in high yield.

Having established the high quality of the library, it was screened against the DNA-binding domain of p53, an important transcription factor that regulates a variety of genes involved in cell cycle control and apoptosis. More than half of human cancers express inactive p53 due to the presence of missense mutations in the DNA-binding domain that destabilize the folding of the protein (Levine, A J. et al. *Nat. Rev. Cancer,* 9, 749-758 (2009)). There is considerable interest in the identification of "chemical chaperones" whose binding to p53 might stabilize the wild-type, functional, folded conformation (Brown, C. J., et al. *Nat. Rev. Cancer,* 9, 862-873 (2009)). Since transcription factors are generally considered to be extremely challenging targets for small molecules (Cochran, A G. *Chem. & Biol.,* 7, R85-R94 (2000)), p53 recognition was considered as a stringent test of the utility of this new class of compounds.

Figures 4A, 4B, 4C:
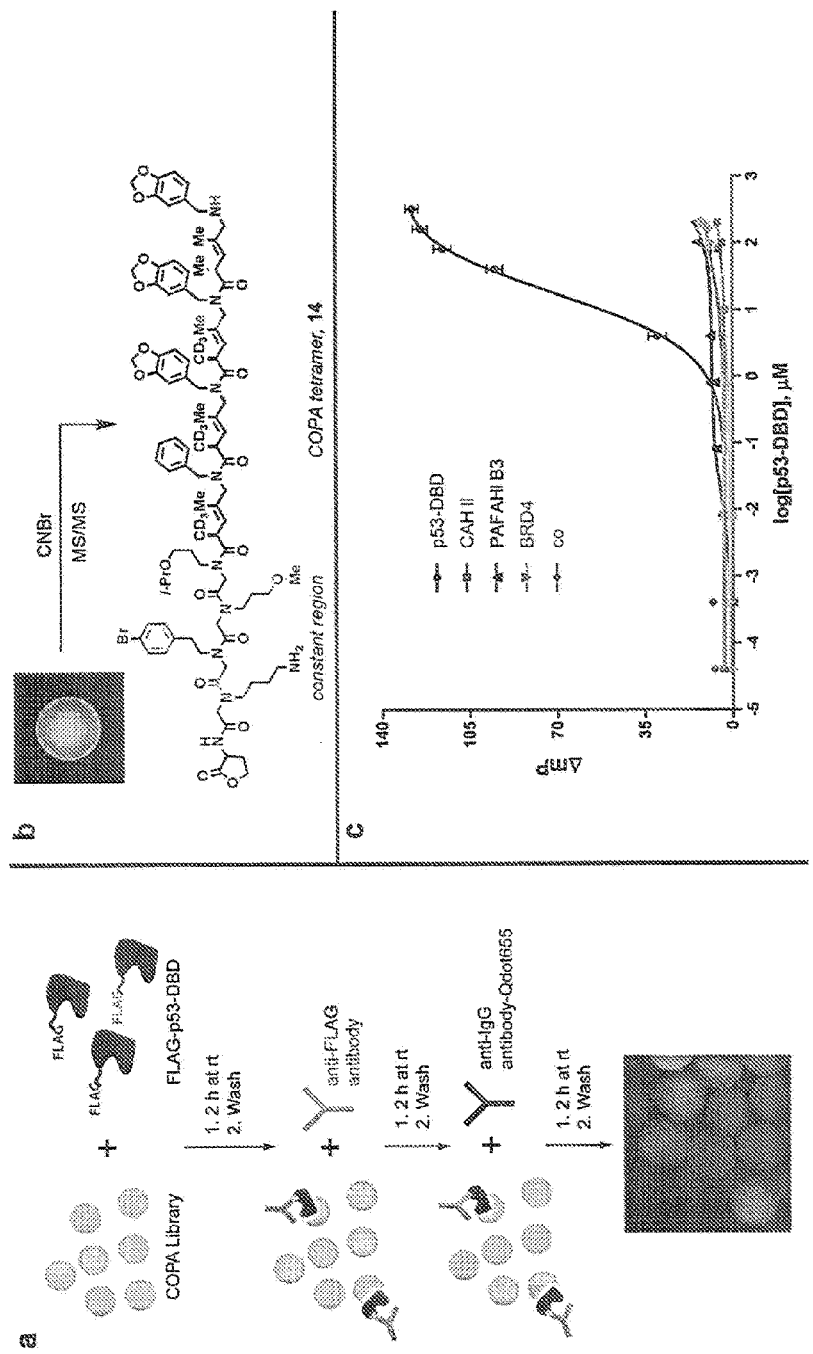
FIGS. 4A-4C are schematic representations showing COPA library, screening, structure elucidation and validation.

Purified, bacterially expressed, FLAG-tagged p53 DBD (10 μM) was incubated with the bead-displayed COPA library in the presence of high levels of competitor proteins to suppress non-specific binding events. The beads were then washed and treated with anti-FLAG antibody followed, after another washing step, by anti-IgG antibodies conjugated to red quantum dots. The beads were then examined under a low power fluorescent microscope. Several beads with a strong red halo surrounding them, indicating binding of the quantum dot via the p53-FLAG/anti-FLAG antibody/anti-IgG-QD sandwich complex, were observed (FIG. 4A). These, as well as some beads with weaker staining, were picked using a micropipette. In all, 22 beads were collected. Six of these putative hits proved to be ligands for either anti-FLAG antibody or the secondary antibody-conjugated quantum dots. The same experiment was done with the peptoid library. In this case, no obvious "hits" with strong red halos were observed, but several more weakly fluorescent beads were picked. The beads were separated in wells of a microtiter plate and released from the bead via CNBr-mediated cleavage of a methionine residue in the linker.

While strong molecular ion peaks were observed in the MALDI mass spectrum for the COPAs, well-defined fragments were not produced in the MS/MS spectrum. Therefore, these molecules were sequenced via tandem ESI mass spectrometry using electron transfer dissociation (ETD) as the fragmentation method (Syka, J. E. P., et al. *Proc. Natl. Acad. Sci. USA,* 101, 9528-9533 (2004)). This proved reasonably successful and the sequences of 8 of the 16 COPA hits could be determined unequivocally. These eight molecules were re-synthesized with a fluorescein tag and tested for binding to p53 by fluorescence anisotropy. Two of the eight COPA molecules showed clear binding to p53. The best of these, compound 14 bound to the p53 DBD with a $K_D$ of approximately 10 μM, but did not bind detectably ($K_D$>500 μM) to two control proteins (FIG. 4C). COPA 14 constitutes the first non-covalent (Lambert, J. M. et al. *Cancer Cell,* 15, 376-388 (2009)) small molecule ligand for the wild-type (Boekler, F. M. et al. *Proc. Natl. Acad. Sci. USA,* 105, 10360-10365 (2008)) p53 DNA-binding domain. The addition of an oligonucleotide that binds p53 tightly did not disrupt the p53-COPA complex, indicating that the synthetic ligand does not recognize the DNA-binding surface of the p53 core domain. The same set of experiments was carried out for the peptoids collected as possible hits in the screening experiment. Not surprisingly, given the low intensity of QD fluorescence observed on the beads, none of the peptoids exhibited binding to the p53 DNA-binding domain ($K_D$s>500 µM). This is interesting in that the COPA and peptoid libraries contained exactly the same amine-derived side chains. This experiment is consistent with the proposition that conformationally constrained COPAs may be superior to peptoids as a source of protein ligands.

In summary, a new class of natural product-inspired oligomeric compounds have been developed that promise to be a valuable source of protein ligands. COPAs are unusual amongst synthetic small molecule oligomers in that they employ concepts long utilized in organic synthesis for acyclic stereo control, such as minimization of A1,3 interactions, to impose significant conformational constraints on the main chain, and subsequent disposition of all main chain substituents in three-dimensional space. In essence, this results in a practical chemical solution to diversity-oriented library construction that couples building block diversity to substantial scaffold diversity (i.e. in the case of a tetrameric COPA that employs antipodes of a common pentenoic acid, 16 distinct and relatively inflexible scaffolds; FIG. 2). This is noteworthy, because the desirability of scaffold diversity in natural product-like libraries has been well documented (Clemons, P. A. et al. *Proc. Natl. Acad. Sci. USA* 107, 18787), and current solutions to this problem require careful synthesis planning to accomplish strategic and divergent reactivity of complex organic intermediates in a library synthesis (Morton, D. et al. *Angew. Chem. Int. Ed.* 48, 104-109 (2009); Luo, T. *J. Am. Chem. Soc.* 131, 5667-5674 (2009); Uchida, T. et al. *Org. Lett.* 11, 1559-1562 (2009)). Further compounding the virtues of COPAs as a chemical foundation to discovery-oriented science, the synthetic strategy described here is completely compatible with split-and-pool solid phase synthesis, making very large libraries readily accessible. Moreover, the highly practical and scalable synthesis of either optically pure antipode of building blocks (i.e. 1), combined with the use of simple primary amines as the source of side chain diversity, allows the synthesis of potentially millions of compounds at a modest cost. Finally, COPA libraries synthesized on hydrophilic TENTAGEL beads can be employed in a variety of inexpensive, yet powerful, binding screens (Xiao, X. et al., *J. Comb. Chem.* 9, 592-600 (2007); Reddy, M. M. et al. *Cell*, 144, in press (2011); Udugamasooriya, D. G. et al., *J. Am. Chem. Soc.* 130, 5744-5752 (2008)) hence eliminating the requirement of substantial infrastructure to maintain diverse compound collections for use in traditional high-throughput screening. Further developments of this technology will explore the power of this chemistry in combination with available on-bead screening technologies as a platform for the discovery of bioactive synthetic molecules.

Example 2: COPA Library Design and Synthesis

Figure 5:
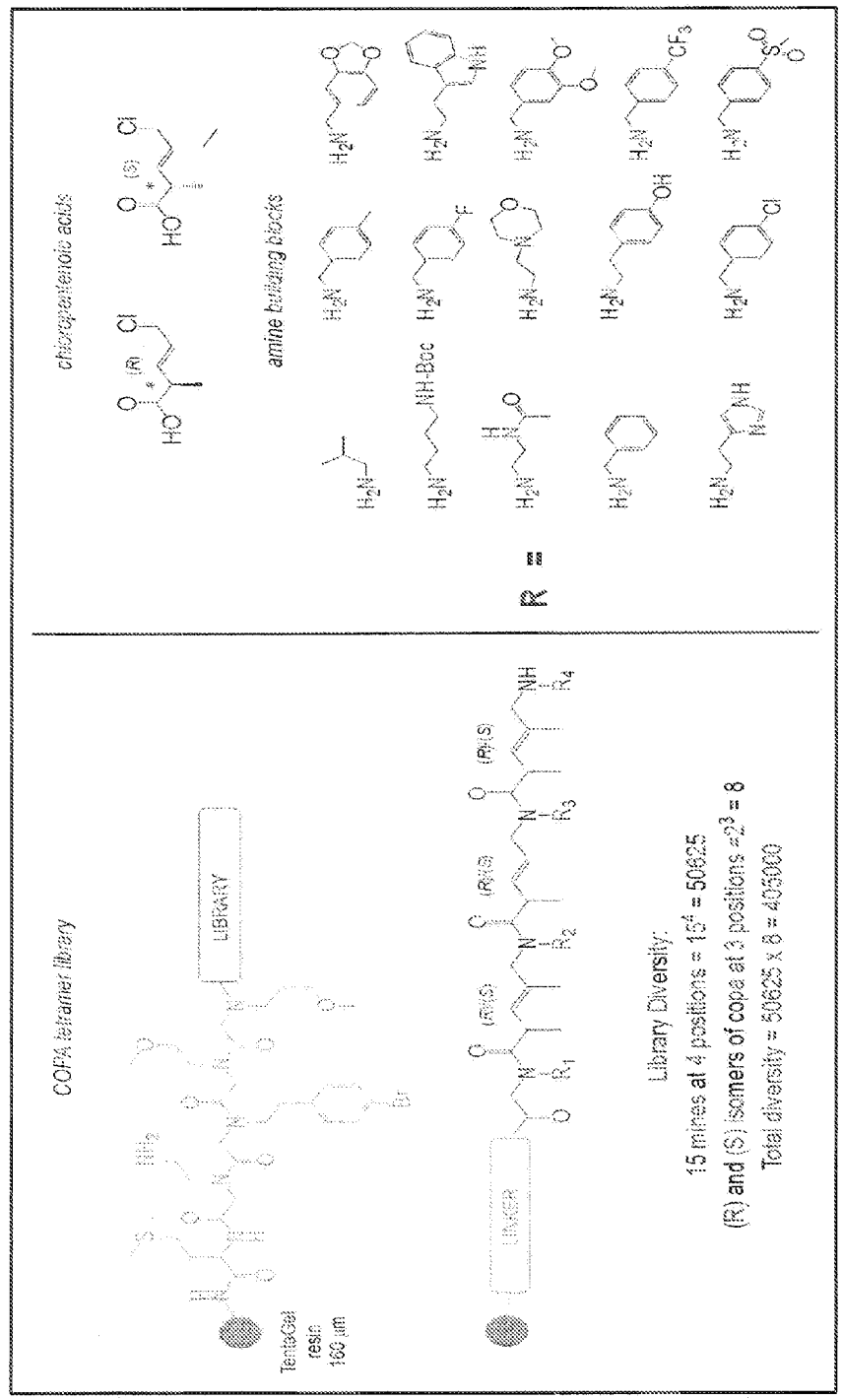
FIG. 5 is a schematic representation showing the general structure of a COPA library synthesized from chloropentanoic acids (R and S configurations) and amine building blocks shown on right.

The COPA library was synthesized on TENTAGEL resin (1.0 g, ~520,000 beads/g, 0.55 mmol/g loading capacity) from Rapp Polymere GmbH, Germany. The approximate total number of beads used to synthesize the library was 520000, which was enough to get at least one copy of each library member (total number of beads/library diversity, 520000/405000=1.28). A COPA library was synthesized on resin following the established one-bead-one-compound split and pool technique (Lam K. S. et al. *Nature* 354, 82-84, (1991)). Fifteen amines (as shown in FIG. 5) were used at four positions. With COPA (S) and (R) isomers at three different positions, the total diversity of the library was 405000. A polyamide linker (FIG. 5) was synthesized first on TENTAGEL MB $NH_2$ resin (160 µm) following standard solid-phase peptide synthesis and microwave assisted sub-monomer protocols (Zuckermann, R. N., et al., *J. Am. Chem. Soc.* 114, 10646-10647 (1992); Olivos, H. J., Alluri, P. G., Reddy, M. M., Salony, D. & Kodadek, T. *Org Lett* 4, 4057-4059, (2002)). To avoid the artifacts of the MALDI-TOF MS, MALDI matrix, and tandem MS/MS with low molar mass compounds a longer linker was designed. Met residue was used to allow the cleavage of the compound from TENTAGEL™ resin by CNBr treatment. A positively charged amino side chain was used to increase the ionization mobility in mass spectrometry. The amine, 4-bromophenylethylamine, was used to help differentiate the sets of signals derived from N-terminal product ions which appeared as singlet and the C-terminal product ions which appeared as doublet due the isotopic pattern of bromine present in the fragments.

TENTAGEL resins (1.0 g, 0.55 mmol) were swelled in anhydrous DMF for 1 h. The beads were treated with 5 equiv of HOBt (1.04 g, 2.75 mmol), 5 equiv of HBTU (1.04 g, 2.75 mmol), 5 equiv of N-methyl morpholine (277.7 µL, 2.75 mmol) and 5 equiv of Fmoc-Met-(OH) (1.02 g, 2.75 mmol) with gentle shaking at room temperature for 3 h in a 50 mL glass reaction vessel from ChemGlass. The beads were washed thoroughly with DMF. The Fmoc group was removed by treating resin with 20% piperidine in DMF for 20 min (2×). The beads were thoroughly washed with DMF. The rest of the linker peptoid was synthesized using microwave assisted solid phase sub-monomer methods for peptoid synthesis using boc-diaminoethane, 4-Br-pehenthylamine, methoxyethylamine and methoxy propylamine.

For library synthesis TENTAGEL™ beads with linker were treated with 20 mL of 1 M bromoacetic acid and 1 M diisopropyl carbodiimide and microwave for 15 sec twice (10% power level) before splitting them equally to distribute into 15 reaction vessels for amine displacement. Each of the vessels were treated with one of 15 amines (1 M in DMF, 2 mL) and subjected to microwave for 15 sec twice (10% power level). The beads were washed with DMF (5×) and split equally to distribute into 2 reaction vessels and subjected to the coupling of (R)- or (S)-COPA isomers. Each vessel with 500 mg of resins was treated with 7 equiv of diisopropylcarbodiimide (1.93 mmol), 5 equiv of HOAt (1.38 mmol) and 5 equiv of (R)- (1.38 mmol) or (S)- (1.38 mmol) in 10.0 mL of anhydrous DMF. The coupling was carried out at 37° C. for 3 h with gentle shaking. Beads were thoroughly washed with DMF and pooled together and mixed well before subjecting them to amine displacements. The beads were split equally to distribute into 15 reaction vessels (0.037 mmol in each vessel) and each of which was treated with 2.0 mL of 1 M solution of one of 15 amines. The reaction was carried out at 37° C. for 3 h with gentle shaking. The beads were thoroughly washed with DMF pooled together and mixed thoroughly. The acylation reaction with COPA (R) and (S), and displacement reaction with 15 amines were repeated two more times to synthesize 4-mer COPA library. The side chain protecting groups were removed by treating pooled resins with 20 mL of 94% trifluoroacetic acid (TFA), 2% triisopropylsilane (TIS), 2% thioanisole and 2% water with gentle shaking for 2 h at room temperature. The resins were washed with DCM thoroughly, dried under vacuum and stored at −20° C.

Expression and Purification of Recombinant CLL Monoclonal Antibodies:

Purified CLL monoclonal antibodies used in screening were obtained from professor Nicholas Chiorazzi's (The Feinstein Institute for Medical Research, North Shore-Long Island Jewish Health System, Manhasset, N.Y.). The heavy chain and light chain were cloned separately and both plasmids were transiently transformed with 293A HEK (human embryonic kidney) fibroblasts (Catera R., et al., *Mol. Med.* 14 (11-12) 665-674 (2008)). The cells were cultured in DMEM supplemented with 10% ultra-low IgG FCS (GIBCO) and co-transfected with 12.5 μg of IgH and IgL chain encoding plasmid DNA by calcium phosphate precipitation. 8-12h after transfection cells were washed with serum-free DMEM and thereafter cultured in DMEM supplemented with 1% Nutridoma SP (Roche). Supernatants were collected after 8 days of culture. For self-reactivity HEp-2 ELISAs and IFAs antibodies were purified on protein G SEPHAROSE™ (Amersham Pharmacia Biosciences). CLL mAbs used in the screening of COPA libraries are listed below.

| CLL-mAb | subset | IgHV | IgH GenBank |
|---------|--------|------|-------------|
| 14 | 9 | 1-69 | AF021951 |
| 068 | 6 | 1-69 | AY553640 |
| 169 | NA | 3-33 | AY055480 |
| 183 | 4 | 4-34 | AF021948 |

Figure 6:
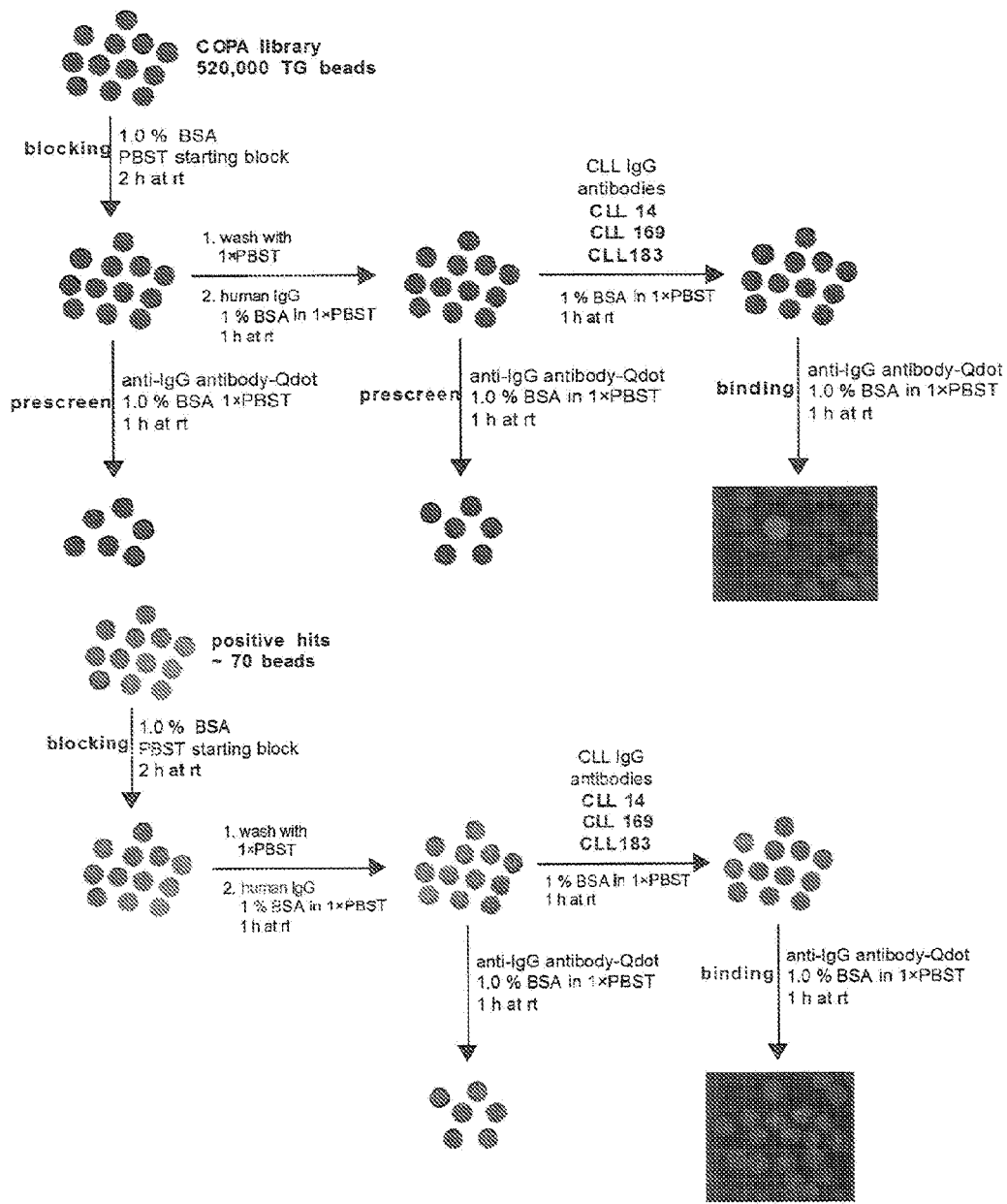
FIG. 6 is a schematic representation of the screening of a COPA library against CLL monoclonal antibodies (mAbs). (left) COPA library was first screened against Goat-antihu-IgG-Qdot 655 and against total human IgG to reduce the possibility of false positives before binding with CLL-mAbs. A total of 70 fluorescent beads were isolated from initial screening. (right). Positive beads from initial screening were subjected to binding again with pooled human IgG. Any fluorescent beads were removed and the rest of the beads were revalidated for binding with CLL-mAbs. A total of 28 beads with intense red fluorescent color were collected for further processing.

Library Screening:

The TENTAGEL resins displaying COPA library (1.0 g) were swollen in DMF for 1 h, washed with DMF (5×), washed extensively with $_{dd}H_2O$ and incubated with water overnight at room temperature (rt). The resins were washed with 1×PBST (5×) and equilibrated with 1×PBST for 4 h at rt. The resins were incubated with blocking buffer (1% BSA in Starting Block PBS Blocking Buffer from Thermoscientific) for 2 h at rt and washed with 1×PBST (3×) before subjecting them to 3-stage screening processes as shown in FIG. 6. First prescreen was carried out using secondary antibody (Goat anti-human-IgG conjugated to Quantum dot 655 from Life Technologies). A 1 to 250 dilution of the antibody was incubated with the resin in 1×PBST containing 1% BSA for 1 h at rt. Resins were visualized under a fluorescence microscope (Olympus BX-51 equipped with a 10×DAPI filter) and any bead that emitted red fluorescence light was removed. All non-fluorescent beads were pooled together and washed with 1×PBST and incubated with total human-IgG (Invitrogen, 5 mg/mL stock) with 1 to 250 dilution in 1×PBST for 1 h at rt. Any unbound human-IgG (huIgG) was removed by washing resins with 1×PBST (3×) and the resins were treated with Goat anti-human-IgG conjugated to Quantum dot 655 (1 to 250 dilution). Beads emitting red fluorescence light were removed and all non-fluorescent beads pooled together and washed with 1×PBST.

The pre-screened resin beads were treated with 1% SDS at 90° C. for 10 min to remove any bound proteins, washed with water (10×) and 1×PBST (5×) and incubated in 1×PBST for 4 h at rt. To minimize nonspecific binding beads were then washed with 1×PBST (3×) and equilibrated in Starting Block PBS Blocking Buffer (from Thermoscientific) containing 1% BSA for 2 h at rt. The resins were washed with 1×PBST (3×) and incubated with recombinant CLL (chronic lymphocytic leukemia) monoclonal antibodies (CLL-mAbs) with a concentration of 150 nM in 1×PBST containing 1% BSA. Three CLL-mAbs (CLL-14, CLL-169 and CLL-183) were used (150 nM each) for binding with beads for 1 h at rt. Any unbound CLL-mAbs were removed by washing resins with 1×PBST (3×) and the beads were incubated with Goat anti-human-IgG conjugated to Quantum dot 655 (1 to 250 dilution) for 1 h at rt. The beads were washed with 1×PBST and visualized under a fluorescence microscope for any bead emitting red fluorescent light. Seventy positive beads with intense red fluorescent color were isolated manually, washed with 1×PBST, treated with 1% SDS for 10 min at 90° C. to remove any bound protein, washed with ddH$_2$O (10×), 1×PBST and incubated in 1vPBST for 4 h. All seventy positive beads were subjected to another round of binding with total human-IgG and CLL-mAbs, respectively, following methods described above. A total of 28 beads with intense fluorescent color were collected as positive hits.

A second 4-mer COPA-C1AA library ($1^{st}$ two positions with chloroacetic acid $3^{rd}$ position with COPA and $4^{th}$ position with chloroacetic acid, with same 15 amine building blocks as shown in FIG. 5) was screened following the way described above against CLL-mAbs 068 and 183.

Sequence Identification:

All positive beads were pooled together and treated with 1% SDS for 10 min at 90° C. and washed with $_{dd}H_2O$ (10×), DMF (5×) and DCM (5×) and dried under vacuum. The beads were isolated and placed in individual wells of a 96-well plate. The compounds on the beads were released by treating each bead with 20 μL of CNBr solution (50 mg CNBr in 5:4:1 CH$_3$CN:CH$_3$COOH:H$_2$O).

Figure 7:
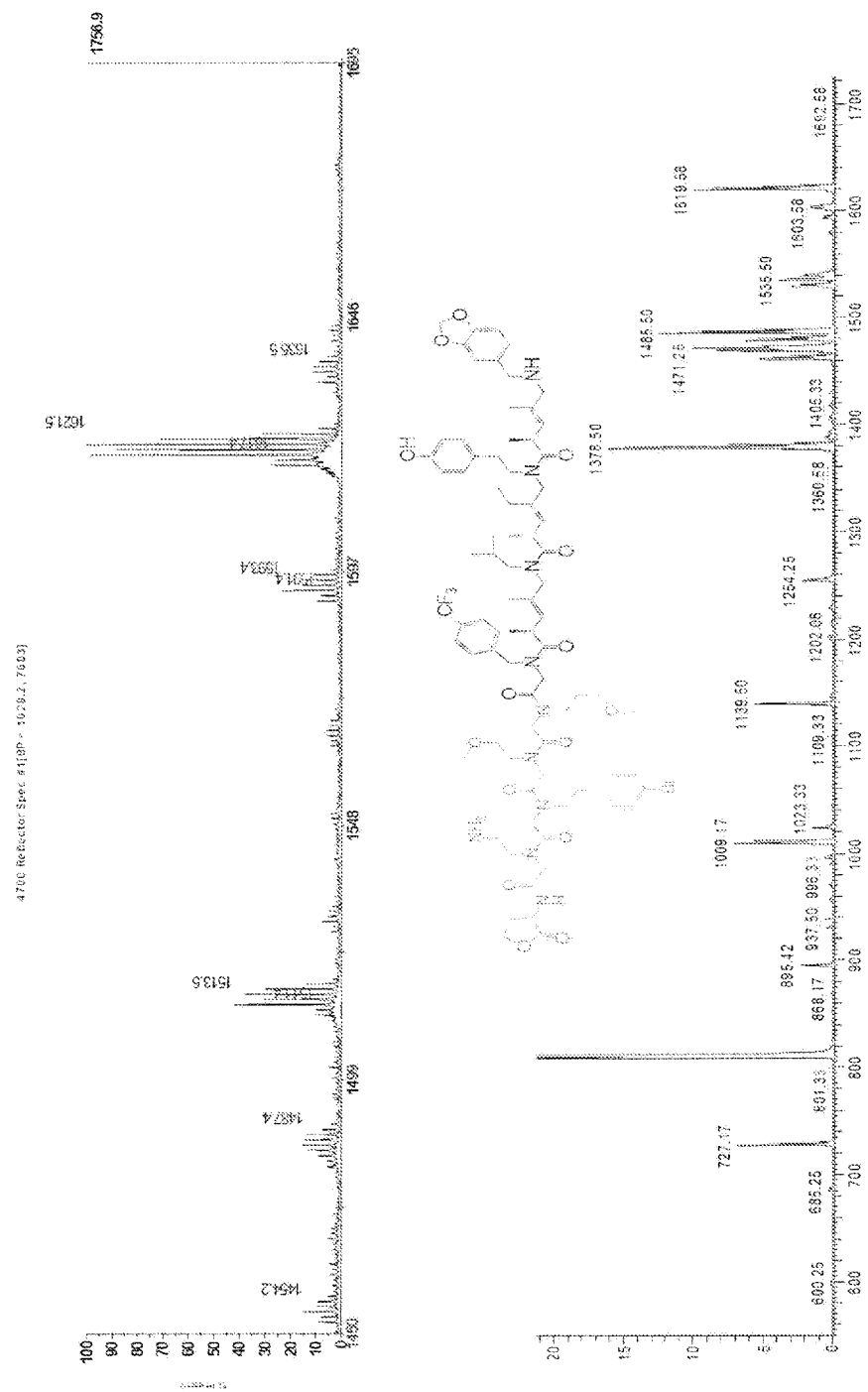
FIG. 7 shows a MALDI-TOF spectrum (top) and LTQ-ETD tandem MS spectrum (bottom) of a positive hit isolated from the screening of a COPA library against CLL-mAbs.

Mass of the each compound was determined by MALDI-TOF mass spectrometry (MALDI-MS 4800Plus from Applied Biosystems) and the sequence of the unknown COPA was determined from sequence specific product ions obtained by electron transfer dissociation (ETD) of the $[M+2H]^{2+}$ and $[M+3H]^{3+}$ precursor ions using Electrospray Ionization (ESI) Linear Ion Trap mass spectrometer (LTQ-ETD; ThermoFinnigan, San Jose, Calif.). The sequences of 24 out of 28 COPA compounds were decoded unequivocally. A representative MALDI-TOF spectrum and ETD spectrum are shown in FIG. 7.

Figure 8:
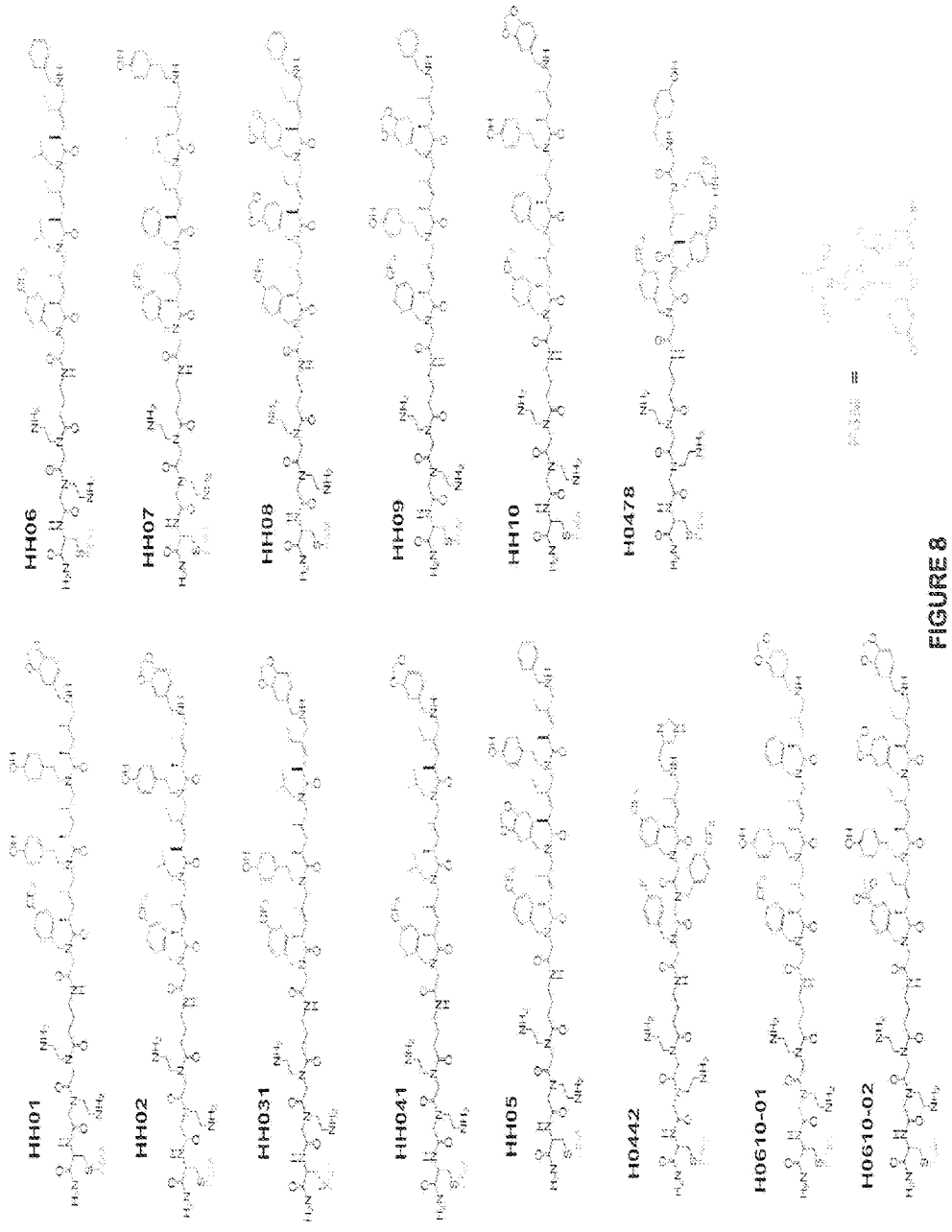
FIG. 8 shows the structure of the resynthesized positive hits isolated from the screening of COPA library against CLL-mAbs. H0442 and H0478 were obtained from the screening of a second library (ClAA-COPA-ClA library) against CLL-mAbs 068 and 183.

Resynthesis of Positive Hits:

A total of 12 positive hits from $1^{st}$ library (screened against CLL-mAbs 14, 169 and 183) and 2 positive hits from $2^{nd}$ library (screened against CLL-mAb 068 and 183) were resynthesized with a fluorophore tag for the validation of binding by fluorescence polarization assay. Each of the compounds was synthesized on 50 mg of Rink-amide resin (0.75 mmol loading capacity, from NovaBiochem) with a linker (as shown in FIG. 8) containing an Fmoc-protected cysteine. Fmoc group was removed by treating resin with 20% piperidine in DMF for 20 min twice. The resins were washed with DMF thoroughly and incubated in 0.2 M DTT (dithiothreitol) in DMF for 10 min in order to reduce the disulfide bonds that could be formed by oxidation of Cys side chain. The beads were washed with DMF thoroughly to remove the DTT completely and treated with 1.3 equiv Fluorescein-5-maleimide (F5M, Thermoscientific) in 2 mL DMF for 4 h at rt in the dark. The beads were washed with DMF to remove the unreacted F5M and DCM thoroughly and dried under vacuum. To remove the fluorophore-tagged compounds Rink resins were treated with 94% TFA, 2% TIS, 2% thioanisole and 2% water for 1 h at room temperature. The cleavage cocktail was removed from the compounds by using an argon flow and by using a high capacity Savant SpeedVac system (Explorer 2000) from Thermoelectron Corp. COPA compounds were then purified on a WATERS-1525 Binary HPLC system (equipped with Waters 1525 binary HPLC pumps and a 2487 dual λ absorbance detector) with CH$_3$CN:H$_2$O gradient (5 to 80% acetonitrile over 30 min run) using Vydac C18 Reverse-phase preparative column. The fractions containing the F5M-conjugated compounds (confirmed by MALDI-TOF) were pooled together and lyophilized using Virtis Benchtop K (Model 4KBTZL) Lyophilizer.

Figure 9:
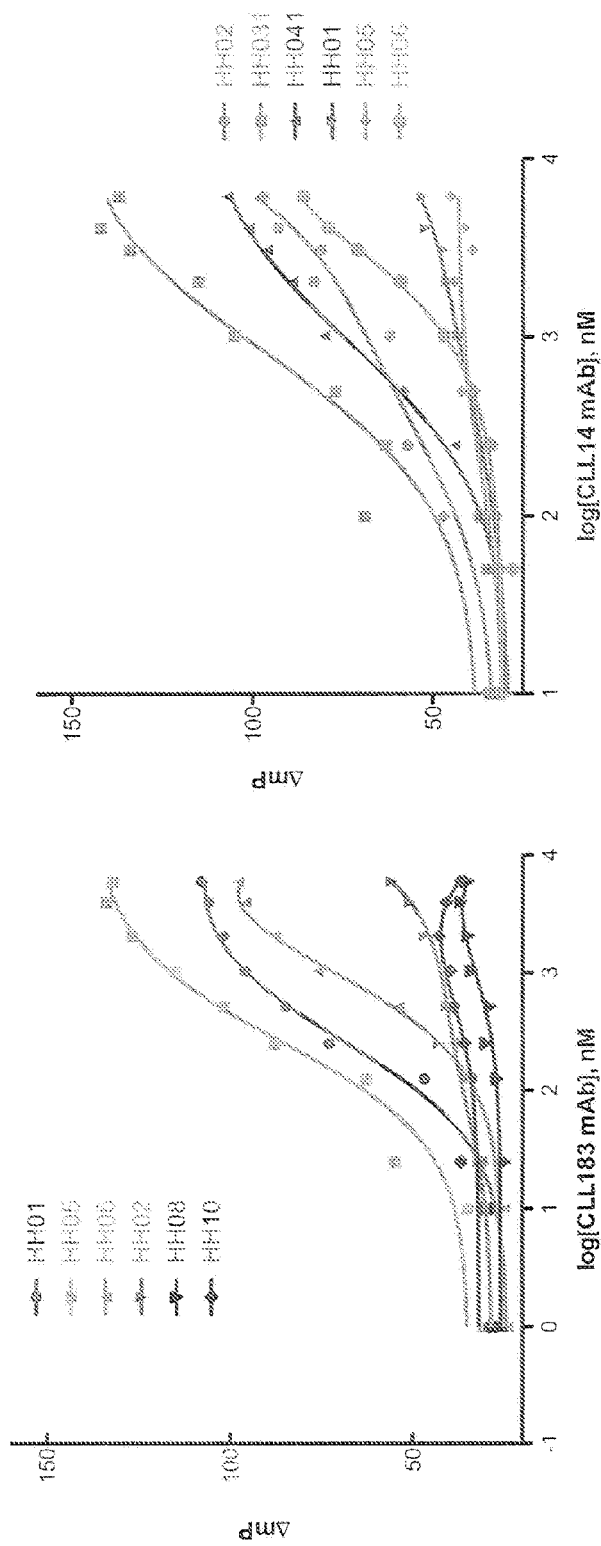
FIG. 9 shows the fluorescence polarization assay for the COPA positive hits. The fluorescein-conjugated COPA compounds (10 nM) were incubated with increasing concentrations (1 nM to 4 µM) of CLL-mAbs for 1 h at room temperature in the dark and the fluorescence polarization was measured using Envision Multilabel Reader (2104) from Perkin Elmer using excitation and emission wavelengths at 495 nm and 535 nm, respectively.

Fluorescence Polarization (FP) Assay:

The FP assay was performed by titrating fluorophore-conjugated COPA compounds (10 nM) with increasing concentrations of CLL-mAbs (from 1 nM to 4 µM) in 1×PBS (pH 7.4) in a 10 µL total volume in a 384-well plate (from Greiner Bio-one, 784076). The compounds were incubated with CLL-mAbs for 1 h in the dark at rt before measuring the fluorescence polarization using Envision Multilabel Reader (2104) from Perkin Elmer using excitation and emission wavelengths at 495 nm and 535 nm, respectively. The $K_D$ value was determined by fitting the curve in a non-linear regression method using equation, $y=[x/(K_D+x)](y_{max}-y_{min})+y_{min}$, using GraphPad Prism 5.0 (GraphPad Software, San Diego, Calif.). COPA oligomers those were detected to show binding affinities (FIG. 9) with CLL-mAbs are listed in the table below.

| mAbs | COPA hits | | | |
|---|---|---|---|---|
| CLL183 | HH01 | HH05 | HH06 | H0442 |
| CLL14 | HH02 | HH031 | HH041 | HH06 |
| CLL068 | H0601 | | | |
| CLL169 | none | | | |

Example 3: COPA Ligands

The COPA ligands for the CLL antibodies may be useful in two ways: diagnostic and therapeutic.

For diagnostic purposes, the molecules will be immobilized on an appropriate analytical platform, such as an ELISA plate and pass either CLL or control sera over it. The amount of antibody retained will be measured by subsequent incubation with a labeled secondary antibody. This will allow for the measuring of the levels of antibodies that bind to a particular COPA and this may provide a serum test for CLL. Since different CLL patients can have different antibodies, a multiplexed ELISA-like assay for this purpose can be developed in which peptoids against a variety of different CLL antibodies are employed. At present the inventors have ligands against three of them and will work to obtain ligands to the other≈12 major types of CLL antibodies present in patients. The idea would be that if any one of COPAs captured significant amounts of antibodies, then the diagnosis would be CLL.

COPAs can be attached to ELISA plates by a variety of methods. It is possible that they could be physisorbed to the plate, though this might compromise their binding to the antibody. Derivatives with a C-terminal cysteine could be attached covalently and specifically to maleimide-activated plates. Finally, the COPA could be conjugated to a carrier protein such as bovine serum albumin (BSA) and this small molecule-protein conjugate could be physically absorbed to the plastic plate.

There are a variety of other analytical platforms that the COPAs could be mounted on to create multiplexed assays, such as Luminex beads (Luminexcorp, Austin Tex.) or an Aushon plate (Aushon BioSystems, Inc., Billerica, Mass.).

As an alternative diagnostic modality, a fluorescently-labeled COPA molecule could be mixed with blood cells from case or control patients and then fluorescence activated cell sorting (FACS) analysis could be employed to determine the level of reactive B cells in the blood.

Figure 10:
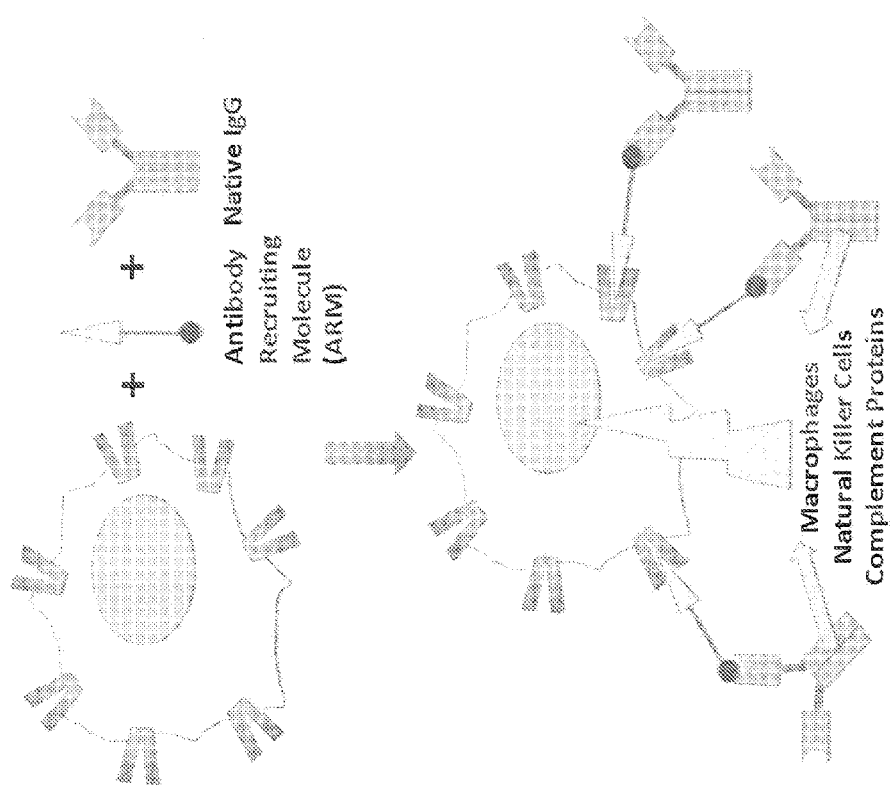
FIG. 10 is a schematic representation showing how small molecules (green triangles) that target the BCR (blue V shape) of CLL cells could be employed to eradicate these cells selectively. This would involve the conjugation of the BCR targeting molecules to a different small molecule that would recruit native antibodies. Alternatively, the BCR-targeting molecule could be pre-conjugated to a recombinant antibody.

With respect to therapeutic value, these compounds could be used as "magic bullets" to deliver toxic cargo to the CLL cells that display the B cell receptor (BCR) corresponding to the antibody on their surface (see FIG. 10). There are several ways this could be done. One is to conjugate the BCR-binding COPA to a small molecule that would recruit native antibodies to the CLL B cells (see FIG. 10). These antibodies would then be expected to recruit the killing machinery of the immune system, such as complement, natural killer cells and macrophages. This would result in the selective eradication of the CLL cells without undue toxicity to non-target cells. Dinitrophenol (DNP) derivatives have been used previously as the native antibody-recruiting molecules and DNP conjugates containing small molecules that bind selectively to cancer cells have been shown to mediate selective cell killing ex vivo (Murelli R. P., et al., *Journal of the American Chemical Society* 131, 17090-17092 (2009)). In a similar vein, the BCR-binding COPA molecule could be tethered to a recombinant antibody (see, for example, Rader C. et al., *Proc Natl Acad Sci USA* 100, 5396-5400 (2003)) and this preformed conjugate could be used as the therapeutic.

What is claimed:

1. A method of synthesizing a chiral monomer of formula (1)

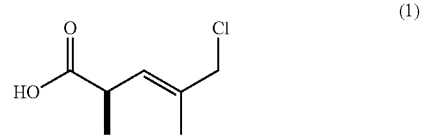

comprising:

N-acylating a chiral oxazolidinone of formula (4)

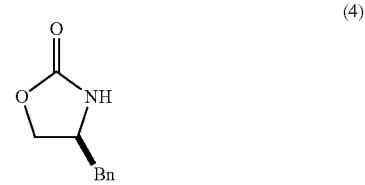

wherein Bn is benzyl, and the compound of formula (4) is a chiral form, by contacting (4) with propionic acid in the presence of ethyl chloroformate, N-methylmorpholine, and LiCl in THF, to provide a chiral N-acyloxazolidinone of formula (5)

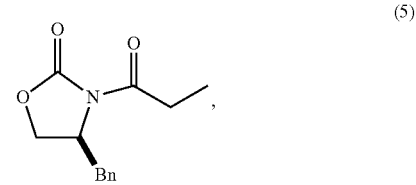 [SMILES: CCC(=O)N1C(=O)OC[C@@H]1Cc1ccccc1]

then, reacting the chiral N-acyloxazolidinone of formula (5) and an α-substituted, α,β-unsaturated aldehyde of formula (6)

(6)

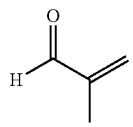

via a magnesium halide catalyzed stereoselective reaction comprising contacting (5) and (6) with MgBr$_2$ and NaSbF$_6$ in ethyl acetate, followed by trimethylsilylchloride to yield a chiral silylated allylic alcohol product of formula (7)

(7)

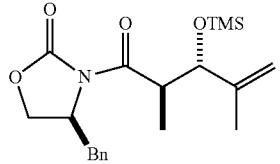

wherein TMS is trimethylsilyl, then,
reacting the chiral silylated allylic alcohol (7) with NbCl$_5$ in dioxane solvent to yield a stereodefined allylic chloride of formula (8)

(8)

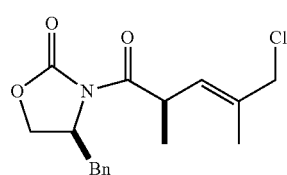

by a stereoselective halogenation reaction that proceeds via stereoselective allylic transposition; then,
hydrolyzing the oxazolidine group to produce a chiral monomer of formula (1)

(1)

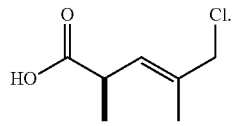

2. The method of claim 1 further comprising a method wherein two monomers of formula (1) are oligomerized,
comprising contacting the compound of formula (1) and secondary amine pyrrolidine (9) in the presence of ethyl chloroformate and N-methylmorpholine in THF to provide a chiral chloroamide of formula (10)

(10)

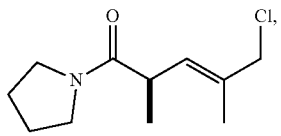

then, coupling the chloroamide of formula (10) and primary amine benzylamine in the presence of triethylamine in THF to provide a chiral allylic amine of formula (11)

(11)

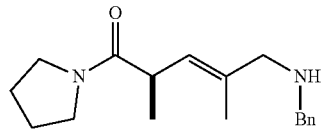

wherein Bn is benzyl, then,
coupling the compound of formula (11) and the compound of formula (1), in the presence of ethyl chloroformate and N-methylmorpholine in THF to provide the chiral oligomeric pentenoic amide (COPA) of formula (12)

(12)

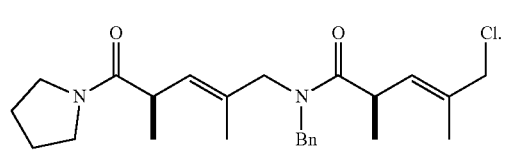

3. A chiral oligomeric pentenoic amide of formula:

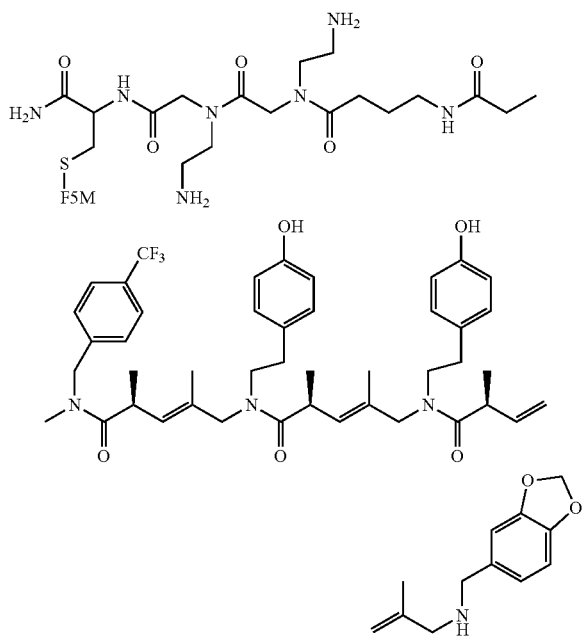

wherein F5M is a Fluorescein-5-maleimide adduct.